United States Patent
Buysse et al.

(10) Patent No.: US 7,963,965 B2
(45) Date of Patent: Jun. 21, 2011

(54) BIPOLAR ELECTROSURGICAL INSTRUMENT FOR SEALING VESSELS

(75) Inventors: Steven P. Buysse, Longmont, CO (US); Dale F. Schmaltz, Fort Collins, CO (US); Gary M. Couture, Longmont, CO (US); Lap P. Nguyen, Longmont, CO (US); Kristin D. Johnson, Louisville, CO (US)

(73) Assignee: Covidien AG, Neuhausen am Rheinfall (CH)

( * ) Notice: Subject to any disclaimer, the term of this patent is extended or adjusted under 35 U.S.C. 154(b) by 1076 days.

(21) Appl. No.: 11/801,618

(22) Filed: May 10, 2007

(65) Prior Publication Data

US 2007/0213712 A1 Sep. 13, 2007

Related U.S. Application Data

(63) Continuation of application No. 10/736,180, filed on Dec. 15, 2003, now Pat. No. 7,241,296, which is a continuation of application No. 10/113,745, filed on Apr. 1, 2002, now Pat. No. 6,726,686, which is a continuation-in-part of application No. 10/090,081, filed on Mar. 1, 2002, now Pat. No. 6,743,229, which is a continuation of application No. 09/502,933, filed on Feb. 11, 2000, now Pat. No. 6,352,536, which is a continuation of application No. 08/968,779, filed on Nov. 12, 1997, now Pat. No. 6,187,003.

(51) Int. Cl.
*A61B 18/12* (2006.01)
(52) U.S. Cl. ........................... 606/51; 606/41
(58) Field of Classification Search .................... 606/41, 606/51
See application file for complete search history.

(56) References Cited

U.S. PATENT DOCUMENTS

| 371,664 A | 10/1887 | Brannan et al. |
| 702,472 A | 6/1902 | Pignolet |
| 728,883 A | 5/1903 | Downes |
| 1,586,645 A | 6/1926 | Bierman |
| 1,813,902 A | 7/1931 | Bovie |
| 1,822,330 A | 9/1931 | Ainslie |
| 1,852,542 A | 4/1932 | Sovatkin |
| 2,002,594 A | 5/1935 | Wappler et al. |
| 2,011,169 A | 8/1935 | Wappler |

(Continued)

FOREIGN PATENT DOCUMENTS

CA 2104423 2/1994

(Continued)

OTHER PUBLICATIONS

International Search Report EP98957771 Dated Aug. 9, 2001.

(Continued)

*Primary Examiner* — Roy D Gibson

(57) ABSTRACT

A bipolar electrosurgical instrument has opposable seal surfaces on its jaws for grasping and sealing vessels and vascular tissue. Inner and outer instrument members allow arcuate motion of the seal surfaces. An open lockbox provides a pivot with lateral support to maintain alignment of the lateral surfaces. Ratchets on the instrument members hold a constant closure force on the tissue during the seal process. A shank portion on each member is tuned to provide an appropriate spring force to hold the seal surfaces together. During surgery, the instrument can be used to grasp and clamp vascular tissue and apply bipolar electrosurgical current through the clamped tissue. In one embodiment, the seal surfaces are partially insulated to prevent a short circuit when the instrument jaws are closed together. In another embodiment, the seal surfaces are removably mounted on the jaws.

13 Claims, 5 Drawing Sheets

U.S. PATENT DOCUMENTS

| | | |
|---|---|---|
| 2,031,682 A | 2/1936 | Wappler et al. |
| 2,054,149 A | 9/1936 | Wappler |
| 2,176,479 A | 10/1939 | Willis |
| 2,305,156 A | 4/1941 | Grubel |
| 2,279,753 A | 4/1942 | Knopp |
| 2,327,353 A | 8/1943 | Karle |
| 2,632,661 A | 8/1948 | Cristofv |
| 2,668,538 A | 2/1954 | Baker |
| 2,796,065 A | 6/1957 | Kapp |
| 3,073,311 A | 1/1963 | Tibbs et al. |
| 3,372,288 A | 3/1968 | Wigington |
| 3,459,187 A | 8/1969 | Pallotta |
| 3,643,663 A | 2/1972 | Sutter |
| 3,648,001 A | 3/1972 | Anderson et al. |
| 3,651,811 A | 3/1972 | Hildebrandt et al. |
| 3,678,229 A | 7/1972 | Osika |
| 3,720,896 A | 3/1973 | Beierlein |
| 3,763,726 A | 10/1973 | Hildebrand |
| 3,779,918 A | 12/1973 | Ikeda et al. |
| 3,801,766 A | 4/1974 | Morrison, Jr. |
| 3,862,630 A | 1/1975 | Balamuth |
| 3,863,339 A | 2/1975 | Reaney et al. |
| 3,866,610 A | 2/1975 | Kletschka |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 3,970,088 A | 7/1976 | Morrison |
| 3,987,795 A | 10/1976 | Morrison |
| 4,005,714 A | 2/1977 | Hiltebrandt |
| 4,016,881 A | 4/1977 | Rioux et al. |
| 4,041,952 A | 8/1977 | Morrison, Jr. et al. |
| 4,043,342 A | 8/1977 | Morrison, Jr. |
| 4,074,718 A | 2/1978 | Morrison, Jr. |
| 4,076,028 A | 2/1978 | Simmons |
| 4,080,820 A | 3/1978 | Allen |
| 4,088,134 A | 5/1978 | Mazzariello |
| 4,112,950 A | 9/1978 | Pike |
| 4,127,222 A | 11/1978 | Adams |
| 4,128,099 A | 12/1978 | Bauer |
| 4,165,746 A | 8/1979 | Burgin |
| 4,187,420 A | 2/1980 | Piber |
| 4,233,734 A | 11/1980 | Bies |
| 4,236,470 A | 12/1980 | Stenson |
| 4,300,564 A | 11/1981 | Furihata |
| 4,311,145 A | 1/1982 | Esty et al. |
| D263,020 S | 2/1982 | Rau, III |
| 4,370,980 A | 2/1983 | Lottick |
| 4,375,218 A | 3/1983 | DiGeronimo |
| 4,416,276 A | 11/1983 | Newton et al. |
| 4,418,692 A | 12/1983 | Guay |
| 4,443,935 A | 4/1984 | Zamba et al. |
| 4,452,246 A | 6/1984 | Bader et al. |
| 4,470,786 A | 9/1984 | Sano et al. |
| 4,492,231 A | 1/1985 | Auth |
| 4,493,320 A | 1/1985 | Treat |
| 4,503,855 A | 3/1985 | Maslanka |
| 4,506,669 A | 3/1985 | Blake, III |
| 4,509,518 A | 4/1985 | McGarry et al. |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,624,254 A | 11/1986 | McGarry et al. |
| 4,655,215 A | 4/1987 | Pike |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,685,459 A | 8/1987 | Xoch et al. |
| 4,733,662 A | 3/1988 | DeSatnick et al. |
| D295,893 S | 5/1988 | Sharkany et al. |
| D295,894 S | 5/1988 | Sharkany et al. |
| 4,754,892 A | 7/1988 | Retief |
| 4,763,669 A | 8/1988 | Jaeger |
| 4,827,929 A | 5/1989 | Hodge |
| 4,829,313 A | 5/1989 | Taggart |
| 4,846,171 A | 7/1989 | Kauphusman et al. |
| 4,887,612 A | 12/1989 | Esser et al. |
| 4,938,761 A | 7/1990 | Ensslin |
| 4,947,009 A | 8/1990 | Osika et al. |
| 4,985,030 A | 1/1991 | Melzer et al. |
| 5,007,908 A | 4/1991 | Rydell |
| 5,026,370 A | 6/1991 | Lottick |
| 5,026,371 A | 6/1991 | Rydell et al. |
| 5,035,695 A | 7/1991 | Weber, Jr. et al. |
| 5,037,433 A | 8/1991 | Wilk et al. |
| 5,042,707 A | 8/1991 | Taheri |
| 5,047,046 A | 9/1991 | Bodoia |
| 5,078,716 A | 1/1992 | Doll |
| 5,084,057 A | 1/1992 | Green et al. |
| 5,085,659 A | 2/1992 | Rydell |
| 5,099,840 A | 3/1992 | Goble et al. |
| 5,100,430 A | 3/1992 | Avellanet et al. |
| 5,108,392 A | 4/1992 | Spingler |
| 5,112,343 A | 5/1992 | Thornton |
| 5,116,332 A | 5/1992 | Lottick |
| 5,147,357 A | 9/1992 | Rose et al. |
| 5,151,102 A | 9/1992 | Xamiyama et al. |
| 5,151,978 A | 9/1992 | Bronikowski et al. |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A | 3/1993 | Parins |
| 5,209,747 A | 5/1993 | Knoepfler |
| 5,211,655 A | 5/1993 | Hasson |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,219,354 A | 6/1993 | Choudhury et al. |
| 5,244,462 A | 9/1993 | Delahuerga et al. |
| 5,250,047 A | 10/1993 | Rydell |
| 5,250,063 A | 10/1993 | Abidin et al. |
| 5,258,001 A | 11/1993 | Corman |
| 5,258,006 A | 11/1993 | Rydell et al. |
| 5,261,918 A | 11/1993 | Phillips et al. |
| 5,275,615 A | 1/1994 | Rose |
| 5,277,201 A | 1/1994 | Stern |
| 5,282,799 A | 2/1994 | Rydell |
| 5,282,800 A | 2/1994 | Foshee et al. |
| 5,282,826 A | 2/1994 | Quadri |
| 5,290,286 A | 3/1994 | Parins |
| 5,300,082 A | 4/1994 | Sharpe et al. |
| 5,304,203 A | 4/1994 | El-Mallawany et al. |
| 5,308,353 A | 5/1994 | Beurrier |
| 5,308,357 A | 5/1994 | Lichtman |
| 5,313,027 A | 5/1994 | Inoue et al. |
| 5,314,445 A | 5/1994 | Degwitz et al. |
| 5,318,589 A | 6/1994 | Lichtman |
| 5,324,289 A | 6/1994 | Eggers |
| D348,930 S | 7/1994 | Olson |
| 5,326,806 A | 7/1994 | Yokoshima et al. |
| 5,330,471 A | 7/1994 | Eggers |
| 5,330,502 A | 7/1994 | Hassler et al. |
| 5,334,183 A | 8/1994 | Wuchinich |
| 5,334,215 A | 8/1994 | Chen |
| 5,336,220 A | 8/1994 | Ryan et al. |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,344,424 A | 9/1994 | Roberts et al. |
| 5,350,391 A | 9/1994 | Iacovelli |
| 5,352,222 A | 10/1994 | Rydell |
| 5,354,271 A | 10/1994 | Voda |
| 5,356,408 A | 10/1994 | Rydell |
| 5,366,477 A | 11/1994 | LeMarie, III et al. |
| 5,368,600 A | 11/1994 | Failla et al. |
| 5,374,277 A | 12/1994 | Hassler |
| 5,376,089 A | 12/1994 | Smith |
| 5,383,875 A | 1/1995 | Bays et al. |
| 5,383,897 A | 1/1995 | Wholey |
| 5,389,098 A | 2/1995 | Tsuruta et al. |
| 5,389,103 A | 2/1995 | Melzer et al. |
| 5,389,104 A | 2/1995 | Hahnen et al. |

| Patent | Date | Inventor |
|---|---|---|
| 5,391,166 A | 2/1995 | Eggers |
| 5,391,183 A | 2/1995 | Janzen et al. |
| 5,396,900 A | 3/1995 | Slater et al. |
| 5,403,312 A | 4/1995 | Yates et al. |
| 5,403,342 A | 4/1995 | Tovey et al. |
| 5,405,344 A | 4/1995 | Williamson et al. |
| 5,409,763 A | 4/1995 | Serizawa et al. |
| 5,411,519 A | 5/1995 | Tovey et al. |
| 5,411,520 A | 5/1995 | Nash et al. |
| 5,413,571 A | 5/1995 | Katsaros et al. |
| 5,415,656 A | 5/1995 | Tihon et al. |
| 5,415,657 A | 5/1995 | Taymor-Luria |
| 5,422,567 A | 6/1995 | Matsunaga |
| 5,423,810 A | 6/1995 | Goble et al. |
| 5,425,690 A | 6/1995 | Chang |
| 5,425,739 A | 6/1995 | Jessen |
| 5,429,616 A | 7/1995 | Schaffer |
| 5,431,672 A | 7/1995 | Cote et al. |
| 5,431,674 A | 7/1995 | Basile et al. |
| 5,437,292 A | 8/1995 | Kipshidze et al. |
| 5,438,302 A | 8/1995 | Goble |
| 5,439,478 A | 8/1995 | Palmer |
| 5,441,517 A | 8/1995 | Kensey et al. |
| 5,443,463 A | 8/1995 | Stern et al. |
| 5,443,464 A | 8/1995 | Russell et al. |
| 5,443,480 A | 8/1995 | Jacobs et al. |
| 5,445,638 A | 8/1995 | Rydell et al. |
| 5,445,658 A | 8/1995 | Durrfeld et al. |
| 5,449,480 A | 9/1995 | Kuriya et al. |
| 5,451,224 A | 9/1995 | Goble et al. |
| 5,454,823 A | 10/1995 | Richardson et al. |
| 5,454,827 A | 10/1995 | Aust et al. |
| 5,456,684 A | 10/1995 | Schmidt et al. |
| 5,458,598 A | 10/1995 | Feinberg et al. |
| 5,460,629 A | 10/1995 | Shlain et al. |
| 5,461,765 A | 10/1995 | Linden et al. |
| 5,462,546 A | 10/1995 | Rydell |
| 5,472,442 A | 12/1995 | Klicek |
| 5,472,443 A | 12/1995 | Cordis et al. |
| 5,478,351 A | 12/1995 | Meade et al. |
| 5,480,406 A | 1/1996 | Nolan et al. |
| 5,480,409 A | 1/1996 | Riza |
| 5,484,436 A | 1/1996 | Eggers et al. |
| 5,496,312 A | 3/1996 | Klicek |
| 5,496,317 A | 3/1996 | Goble et al. |
| 5,496,347 A | 3/1996 | Hashiguchi et al. |
| 5,499,997 A | 3/1996 | Sharpe et al. |
| 5,509,922 A | 4/1996 | Aranyi et al. |
| 5,514,134 A | 5/1996 | Rydell et al. |
| 5,527,313 A | 6/1996 | Scott et al. |
| 5,528,833 A | 6/1996 | Sakuma |
| 5,529,067 A | 6/1996 | Larsen et al. |
| 5,531,744 A | 7/1996 | Nardella et al. |
| 5,536,251 A | 7/1996 | Evard et al. |
| 5,540,684 A | 7/1996 | Hassler, Jr. |
| 5,540,685 A | 7/1996 | Parins et al. |
| 5,540,706 A | 7/1996 | Aust et al. |
| 5,540,715 A | 7/1996 | Katsaros et al. |
| 5,542,945 A | 8/1996 | Fritzsch |
| 5,558,671 A | 9/1996 | Yates |
| 5,558,672 A | 9/1996 | Edwards et al. |
| 5,562,619 A | 10/1996 | Mirarchi et al. |
| 5,562,699 A | 10/1996 | Heimberger et al. |
| 5,562,720 A | 10/1996 | Stern et al. |
| 5,564,615 A | 10/1996 | Bishop et al. |
| 5,569,241 A | 10/1996 | Edwards |
| 5,569,243 A | 10/1996 | Kortenbach et al. |
| 5,571,100 A | 11/1996 | Goble et al. |
| 5,573,424 A | 11/1996 | Poppe |
| 5,573,534 A | 11/1996 | Stone |
| 5,573,535 A | 11/1996 | Viklund |
| 5,575,799 A | 11/1996 | Bolanos et al. |
| 5,575,805 A | 11/1996 | Li |
| 5,578,052 A | 11/1996 | Koros et al. |
| 5,579,781 A | 12/1996 | Cooke |
| 5,582,611 A | 12/1996 | Tsukagoshi et al. |
| 5,582,617 A | 12/1996 | Klieman et al. |
| 5,585,896 A | 12/1996 | Yamazaki et al. |
| 5,590,570 A | 1/1997 | LeMaire, III et al. |
| 5,591,181 A | 1/1997 | Stone et al. |
| 5,597,107 A | 1/1997 | Knodel et al. |
| 5,601,224 A | 2/1997 | Bishop et al. |
| 5,601,601 A | 2/1997 | Tal et al. |
| 5,601,641 A | 2/1997 | Stephens |
| 5,603,711 A | 2/1997 | Parins et al. |
| 5,603,723 A | 2/1997 | Aranyi et al. |
| 5,611,798 A | 3/1997 | Eggers |
| 5,611,808 A | 3/1997 | Hossain et al. |
| 5,611,813 A | 3/1997 | Lichtman |
| 5,620,415 A | 4/1997 | Lucey et al. |
| 5,620,453 A | 4/1997 | Nallakrishnan |
| 5,620,459 A | 4/1997 | Lichtman |
| 5,624,452 A | 4/1997 | Yates |
| 5,626,578 A | 5/1997 | Tihon |
| 5,626,609 A | 5/1997 | Zvenyatsky et al. |
| 5,630,833 A | 5/1997 | Katsaros et al. |
| 5,637,110 A | 6/1997 | Pennybacker et al. |
| 5,638,003 A | 6/1997 | Hall |
| 5,643,294 A | 7/1997 | Tovey et al. |
| 5,647,869 A | 7/1997 | Goble et al. |
| 5,647,871 A | 7/1997 | Levine et al. |
| 5,649,959 A | 7/1997 | Hannam et al. |
| 5,655,650 A | 8/1997 | Naitou |
| 5,658,281 A | 8/1997 | Heard |
| D384,413 S | 9/1997 | Zlock et al. |
| 5,662,667 A | 9/1997 | Knodel |
| 5,665,100 A | 9/1997 | Yoon |
| 5,667,526 A | 9/1997 | Levin |
| 5,674,220 A | 10/1997 | Fox et al. |
| 5,674,229 A | 10/1997 | Tovey et al. |
| 5,681,282 A | 10/1997 | Eggers et al. |
| 5,688,270 A | 11/1997 | Yates et al. |
| 5,690,652 A | 11/1997 | Wurster et al. |
| 5,690,653 A | 11/1997 | Richardson et al. |
| 5,693,051 A | 12/1997 | Schulze et al. |
| 5,693,920 A | 12/1997 | Maeda |
| 5,695,522 A | 12/1997 | LeMaire, III et al. |
| 5,700,261 A | 12/1997 | Brinkerhoff |
| 5,700,270 A | 12/1997 | Peyser et al. |
| 5,702,390 A | 12/1997 | Austin et al. |
| 5,707,369 A | 1/1998 | Vaitekunas et al. |
| 5,709,680 A | 1/1998 | Yates et al. |
| 5,716,366 A | 2/1998 | Yates |
| 5,720,744 A | 2/1998 | Eggleston et al. |
| 5,722,421 A | 3/1998 | Francese et al. |
| 5,725,536 A | 3/1998 | Oberlin et al. |
| 5,727,428 A | 3/1998 | LeMaire, III et al. |
| 5,735,848 A | 4/1998 | Yates et al. |
| 5,743,906 A | 4/1998 | Parins et al. |
| 5,752,973 A | 5/1998 | Kieturakis |
| 5,755,717 A | 5/1998 | Yates et al. |
| 5,759,188 A | 6/1998 | Yoon |
| 5,766,130 A | 6/1998 | Selmonosky |
| 5,766,166 A | 6/1998 | Hooven |
| 5,766,170 A | 6/1998 | Eggers |
| 5,766,196 A | 6/1998 | Griffiths |
| 5,769,849 A | 6/1998 | Eggers |
| 5,772,655 A | 6/1998 | Bauer et al. |
| 5,772,670 A | 6/1998 | Brosa |
| 5,776,128 A | 7/1998 | Eggers |
| 5,776,130 A | 7/1998 | Buysse et al. |
| 5,779,646 A | 7/1998 | Koblish et al. |
| 5,779,701 A | 7/1998 | McBrayer et al. |
| H1745 H | 8/1998 | Paraschac |
| 5,792,137 A | 8/1998 | Carr et al. |
| 5,792,165 A | 8/1998 | Klieman et al. |
| 5,792,177 A | 8/1998 | Kaseda |
| 5,797,537 A | 8/1998 | Oberlin et al. |
| 5,797,927 A | 8/1998 | Yoon |
| 5,797,938 A | 8/1998 | Paraschac et al. |
| 5,797,941 A | 8/1998 | Schulze et al. |
| 5,797,958 A | 8/1998 | Yoon |
| 5,800,449 A | 9/1998 | Wales |
| 5,807,393 A | 9/1998 | Williamson, IV et al. |
| 5,810,764 A | 9/1998 | Eggers et al. |
| 5,810,805 A | 9/1998 | Sutcu et al. |
| 5,810,808 A | 9/1998 | Eggers |
| 5,810,811 A | 9/1998 | Yates et al. |

| | | | | | |
|---|---|---|---|---|---|
| 5,810,877 A | 9/1998 | Roth et al. | 6,077,287 A | 6/2000 | Taylor et al. |
| 5,814,043 A | 9/1998 | Shapeton | 6,080,180 A | 6/2000 | Yoon et al. |
| 5,814,054 A | 9/1998 | Kortenbach et al. | RE36,795 E | 7/2000 | Rydell |
| 5,817,093 A | 10/1998 | Williamson, IV et al. | 6,083,223 A | 7/2000 | Baker |
| 5,817,119 A | 10/1998 | Klieman et al. | 6,086,586 A | 7/2000 | Hooven |
| 5,820,630 A | 10/1998 | Lind | 6,086,601 A | 7/2000 | Yoon |
| 5,824,978 A | 10/1998 | Karasik et al. | 6,090,107 A | 7/2000 | Borgmeier et al. |
| 5,827,271 A | 10/1998 | Buysse et al. | 6,096,037 A | 8/2000 | Mulier et al. |
| 5,827,279 A | 10/1998 | Hughett et al. | 6,099,550 A | 8/2000 | Yoon |
| 5,827,281 A | 10/1998 | Levin | 6,102,909 A | 8/2000 | Chen et al. |
| 5,827,323 A | 10/1998 | Klieman et al. | 6,106,542 A | 8/2000 | Toybin et al. |
| 5,827,548 A | 10/1998 | Lavallee et al. | 6,110,171 A | 8/2000 | Rydell |
| 5,833,690 A | 11/1998 | Yates et al. | 6,113,596 A | 9/2000 | Hooven et al. |
| 5,843,080 A | 12/1998 | Fleenor et al. | 6,113,598 A | 9/2000 | Baker |
| 5,849,022 A | 12/1998 | Sakashita et al. | 6,117,158 A | 9/2000 | Measamer et al. |
| 5,853,412 A | 12/1998 | Mayenberger | 6,122,549 A | 9/2000 | Sharkey et al. |
| 5,859,527 A | 1/1999 | Cook | 6,123,701 A | 9/2000 | Nezhat |
| 5,860,976 A | 1/1999 | Billings et al. | H1904 H | 10/2000 | Yates et al. |
| 5,876,401 A | 3/1999 | Schulze et al. | 6,126,658 A | 10/2000 | Baker |
| 5,876,412 A | 3/1999 | Piraka | 6,126,665 A | 10/2000 | Yoon |
| 5,882,567 A | 3/1999 | Cavallaro et al. | 6,139,563 A | 10/2000 | Cosgrove, III et al. |
| 5,891,141 A | 4/1999 | Rydell | 6,143,005 A | 11/2000 | Yoon et al. |
| 5,891,142 A | 4/1999 | Eggers et al. | 6,152,923 A | 11/2000 | Ryan |
| 5,893,863 A | 4/1999 | Yoon | 6,162,220 A | 12/2000 | Nezhat |
| 5,893,875 A | 4/1999 | O'Connor et al. | 6,171,316 B1 | 1/2001 | Kovac et al. |
| 5,893,877 A | 4/1999 | Gampp, Jr. et al. | 6,174,309 B1 | 1/2001 | Wrublewski et al. |
| 5,897,563 A | 4/1999 | Yoon et al. | 6,178,628 B1 | 1/2001 | Clemens et al. |
| 5,902,301 A | 5/1999 | Olig | 6,179,834 B1 | 1/2001 | Buysse et al. |
| 5,906,630 A | 5/1999 | Anderhub et al. | 6,179,837 B1 | 1/2001 | Hooven |
| 5,908,420 A | 6/1999 | Parins et al. | 6,183,467 B1 | 2/2001 | Shapeton et al. |
| 5,908,432 A | 6/1999 | Pan | 6,187,003 B1 | 2/2001 | Buysse et al. |
| 5,911,719 A | 6/1999 | Eggers | 6,190,386 B1 | 2/2001 | Rydell |
| 5,913,874 A | 6/1999 | Berns et al. | 6,190,400 B1 | 2/2001 | Vandemoer et al. |
| 5,921,916 A | 7/1999 | Aeikens et al. | 6,193,718 B1 | 2/2001 | Kortenbach et al. |
| 5,921,984 A | 7/1999 | Sutcu et al. | 6,206,876 B1 | 3/2001 | Levine et al. |
| 5,925,043 A | 7/1999 | Kumar et al. | 6,206,877 B1 | 3/2001 | Kese et al. |
| 5,928,136 A | 7/1999 | Barry | 6,206,893 B1 | 3/2001 | Klein et al. |
| 5,935,126 A | 8/1999 | Riza | 6,214,028 B1 | 4/2001 | Yoon et al. |
| 5,941,869 A | 8/1999 | Patterson et al. | 6,217,602 B1 | 4/2001 | Redmon |
| 5,944,718 A | 8/1999 | Austin et al. | 6,217,615 B1 | 4/2001 | Sioshansi et al. |
| 5,951,546 A | 9/1999 | Lorentzen | 6,221,039 B1 | 4/2001 | Durgin et al. |
| 5,951,549 A | 9/1999 | Richardson et al. | 6,223,100 B1 | 4/2001 | Green |
| 5,954,720 A | 9/1999 | Wilson et al. | 6,224,593 B1 | 5/2001 | Ryan et al. |
| 5,954,731 A | 9/1999 | Yoon | 6,224,614 B1 | 5/2001 | Yoon |
| 5,954,733 A | 9/1999 | Yoon | 6,228,080 B1 | 5/2001 | Gines |
| 5,957,923 A | 9/1999 | Hahnen et al. | 6,228,083 B1 | 5/2001 | Lands et al. |
| 5,957,937 A | 9/1999 | Yoon | 6,248,124 B1 | 6/2001 | Pedros et al. |
| 5,960,544 A | 10/1999 | Beyers | 6,248,944 B1 | 6/2001 | Ito |
| 5,961,514 A | 10/1999 | Long et al. | 6,261,307 B1 | 7/2001 | Yoon et al. |
| 5,964,758 A | 10/1999 | Dresden | 6,267,761 B1 | 7/2001 | Ryan |
| 5,976,132 A | 11/1999 | Morris | 6,270,497 B1 | 8/2001 | Sekino et al. |
| 5,984,932 A | 11/1999 | Yoon | 6,270,508 B1 | 8/2001 | Klieman et al. |
| 5,984,938 A | 11/1999 | Yoon | 6,273,887 B1 | 8/2001 | Yamauchi et al. |
| 5,984,939 A | 11/1999 | Yoon | 6,277,117 B1 | 8/2001 | Tetzlaff et al. |
| 5,989,277 A | 11/1999 | LeMaire, III et al. | 6,280,458 B1 | 8/2001 | Boche et al. |
| 5,993,466 A | 11/1999 | Yoon | 6,283,961 B1 | 9/2001 | Underwood et al. |
| 5,993,467 A | 11/1999 | Yoon | D449,886 S | 10/2001 | Tetzlaff et al. |
| 5,997,565 A | 12/1999 | Inoue | 6,298,550 B1 | 10/2001 | Kirwan |
| 6,004,332 A | 12/1999 | Yoon et al. | 6,302,424 B1 | 10/2001 | Gisinger et al. |
| 6,004,335 A | 12/1999 | Vaitekunas et al. | 6,319,262 B1 | 11/2001 | Bates et al. |
| 6,010,516 A | 1/2000 | Hulka et al. | 6,319,451 B1 | 11/2001 | Brune |
| 6,017,358 A | 1/2000 | Yoon et al. | 6,322,561 B1 | 11/2001 | Eggers et al. |
| 6,021,693 A | 2/2000 | Feng-Sing | 6,322,580 B1 | 11/2001 | Kanner |
| 6,024,741 A | 2/2000 | Williamson et al. | 6,325,795 B1 | 12/2001 | Lindemann et al. |
| 6,024,743 A | 2/2000 | Edwards | 6,334,860 B1 | 1/2002 | Dorn |
| 6,024,744 A | 2/2000 | Kese et al. | 6,334,861 B1 | 1/2002 | Chandler et al. |
| 6,027,522 A | 2/2000 | Palmer | 6,345,532 B1 | 2/2002 | Coudray et al. |
| 6,030,384 A | 2/2000 | Nezhat | 6,350,264 B1 | 2/2002 | Hooven |
| 6,033,399 A | 3/2000 | Gines | 6,352,536 B1 | 3/2002 | Buysse et al. |
| 6,039,733 A | 3/2000 | Buysse et al. | 6,358,249 B1 | 3/2002 | Chen et al. |
| 6,041,679 A | 3/2000 | Slater et al. | 6,358,259 B1 | 3/2002 | Swain et al. |
| 6,050,996 A | 4/2000 | Schmaltz et al. | 6,358,268 B1 | 3/2002 | Hunt et al. |
| 6,053,914 A | 4/2000 | Eggers et al. | 6,364,879 B1 | 4/2002 | Chen et al. |
| 6,053,933 A | 4/2000 | Balazs et al. | D457,958 S | 5/2002 | Dycus et al. |
| D424,694 S | 5/2000 | Tetzlaff et al. | D457,959 S | 5/2002 | Tetzlaff et al. |
| D425,201 S | 5/2000 | Tetzlaff et al. | 6,387,094 B1 | 5/2002 | Eitenmuller |
| 6,059,782 A | 5/2000 | Novak et al. | 6,391,035 B1 | 5/2002 | Appleby et al. |
| 6,066,139 A | 5/2000 | Ryan et al. | 6,398,779 B1 | 6/2002 | Buysse et al. |
| 6,074,386 A | 6/2000 | Goble et al. | 6,402,747 B1 | 6/2002 | Lindemann et al. |

| | | | |
|---|---|---|---|
| 6,409,728 B1 | 6/2002 | Ehr et al. | |
| H2037 H | 7/2002 | Yates et al. | |
| 6,419,675 B1 | 7/2002 | Gallo, Sr. | |
| 6,425,896 B1 | 7/2002 | Baltschun et al. | |
| 6,432,112 B2 | 8/2002 | Brock et al. | |
| 6,440,144 B1 | 8/2002 | Bacher | |
| 6,443,952 B1 | 9/2002 | Mulier et al. | |
| 6,443,970 B1 | 9/2002 | Schulze et al. | |
| 6,451,018 B1 | 9/2002 | Lands et al. | |
| 6,458,125 B1 | 10/2002 | Cosmescu | |
| 6,458,128 B1 | 10/2002 | Schulze | |
| 6,458,130 B1 | 10/2002 | Frazier et al. | |
| 6,461,352 B2 | 10/2002 | Morgan et al. | |
| 6,461,368 B2 | 10/2002 | Fogarty et al. | |
| 6,464,701 B1 | 10/2002 | Hooven et al. | |
| 6,464,702 B2 | 10/2002 | Schulze et al. | |
| 6,464,704 B2 | 10/2002 | Schmaltz et al. | |
| 6,485,489 B2 | 11/2002 | Teirstein et al. | |
| 6,494,888 B1 | 12/2002 | Laufer et al. | |
| 6,500,176 B1 | 12/2002 | Truckai et al. | |
| 6,506,196 B1 | 1/2003 | Laufer | |
| 6,508,815 B1 | 1/2003 | Strul et al. | |
| 6,511,480 B1 | 1/2003 | Tetzlaff et al. | |
| 6,514,215 B1 | 2/2003 | Ouchi | |
| 6,514,252 B2 | 2/2003 | Nezhat et al. | |
| 6,517,539 B1 | 2/2003 | Smith et al. | |
| 6,527,771 B1 | 3/2003 | Weadock et al. | |
| 6,533,784 B2 | 3/2003 | Truckai et al. | |
| 6,545,239 B2 | 4/2003 | Spedale et al. | |
| 6,558,385 B1 | 5/2003 | McClurken et al. | |
| 6,562,037 B2 | 5/2003 | Paton et al. | |
| 6,569,105 B1 | 5/2003 | Kortenbach et al. | |
| 6,582,450 B2 | 6/2003 | Ouchi | |
| 6,585,735 B1 | 7/2003 | Lands et al. | |
| 6,602,252 B2 | 8/2003 | Mollenauer | |
| 6,605,790 B2 | 8/2003 | Yoshida | |
| 6,616,658 B2 | 9/2003 | Ineson | |
| 6,616,661 B2 | 9/2003 | Wellman et al. | |
| 6,620,161 B2 | 9/2003 | Schulze et al. | |
| 6,620,184 B2 | 9/2003 | De Laforcade et al. | |
| 6,626,901 B1 | 9/2003 | Treat et al. | |
| 6,638,287 B2 | 10/2003 | Danitz et al. | |
| 6,641,595 B1 | 11/2003 | Moran et al. | |
| 6,652,514 B2 | 11/2003 | Ellman et al. | |
| 6,652,521 B2 | 11/2003 | Schulze | |
| 6,656,175 B2 | 12/2003 | Francischelli et al. | |
| 6,656,177 B2 | 12/2003 | Truckai et al. | |
| 6,660,072 B2 | 12/2003 | Chatterjee | |
| 6,663,639 B1 | 12/2003 | Laufer et al. | |
| 6,663,641 B1 | 12/2003 | Kovac et al. | |
| 6,666,854 B1 | 12/2003 | Lange | |
| 6,669,696 B2 | 12/2003 | Bacher et al. | |
| 6,673,092 B1 | 1/2004 | Bacher | |
| 6,676,660 B2 | 1/2004 | Wampler et al. | |
| 6,676,676 B2 | 1/2004 | Danitz et al. | |
| 6,679,882 B1 | 1/2004 | Kornerup | |
| 6,682,527 B2 | 1/2004 | Strul | |
| 6,682,528 B2 | 1/2004 | Frazier et al. | |
| 6,685,724 B1 | 2/2004 | Haluck | |
| 6,689,131 B2 | 2/2004 | McClurken | |
| 6,692,445 B2 | 2/2004 | Roberts et al. | |
| 6,693,246 B1 | 2/2004 | Rudolph et al. | |
| 6,695,840 B2 | 2/2004 | Schulze | |
| 6,702,810 B2 | 3/2004 | McClurken et al. | |
| 6,723,092 B2 | 4/2004 | Brown et al. | |
| 6,726,068 B2 | 4/2004 | Miller | |
| 6,726,686 B2 | 4/2004 | Buysse et al. | |
| 6,726,694 B2 | 4/2004 | Blatter et al. | |
| 6,733,498 B2 | 5/2004 | Paton et al. | |
| 6,736,813 B2 | 5/2004 | Yamauchi et al. | |
| 6,743,229 B2 | 6/2004 | Buysse et al. | |
| 6,743,230 B2 | 6/2004 | Lutze et al. | |
| 6,743,239 B1 | 6/2004 | Kuehn et al. | |
| 6,743,240 B2 | 6/2004 | Smith et al. | |
| 6,755,843 B2 | 6/2004 | Chung et al. | |
| 6,756,553 B1 | 6/2004 | Yamaguchi et al. | |
| 6,757,977 B2 | 7/2004 | Dambal et al. | |
| D493,888 S | 8/2004 | Reschke | |
| 6,770,072 B1 | 8/2004 | Truckai et al. | |
| 6,773,409 B2 | 8/2004 | Truckai et al. | |
| 6,773,432 B1 | 8/2004 | Clayman et al. | |
| 6,773,434 B2 | 8/2004 | Ciarrocca | |
| 6,773,441 B1 | 8/2004 | Laufer et al. | |
| 6,775,575 B2 | 8/2004 | Bommannan et al. | |
| 6,776,780 B2 | 8/2004 | Mulier et al. | |
| 6,786,905 B2 | 9/2004 | Swanson et al. | |
| 6,790,217 B2 | 9/2004 | Schulze et al. | |
| 6,796,981 B2 | 9/2004 | Wham et al. | |
| D496,997 S | 10/2004 | Dycus et al. | |
| 6,800,825 B1 | 10/2004 | Sasaki et al. | |
| 6,802,843 B2 | 10/2004 | Truckai et al. | |
| 6,808,525 B2 | 10/2004 | Latterell et al. | |
| D499,181 S | 11/2004 | Dycus et al. | |
| 6,818,000 B2 | 11/2004 | Muller et al. | |
| 6,821,285 B2 | 11/2004 | Laufer et al. | |
| 6,835,200 B2 | 12/2004 | Laufer et al. | |
| 6,857,357 B2 | 2/2005 | Fujii | |
| 6,860,880 B2 | 3/2005 | Treat et al. | |
| 6,887,240 B1 | 5/2005 | Lands et al. | |
| 6,889,116 B2 | 5/2005 | Jinno | |
| 6,914,201 B2 | 7/2005 | Van Vooren et al. | |
| 6,926,716 B2 | 8/2005 | Baker et al. | |
| 6,929,644 B2 | 8/2005 | Truckai et al. | |
| 6,932,810 B2 | 8/2005 | Ryan | |
| 6,932,816 B2 | 8/2005 | Phan | |
| 6,934,134 B2 | 8/2005 | Mori et al. | |
| 6,936,061 B2 | 8/2005 | Sasaki | |
| D509,297 S | 9/2005 | Wells | |
| 6,942,662 B2 | 9/2005 | Goble et al. | |
| 6,943,311 B2 | 9/2005 | Miyako | |
| 6,953,430 B2 | 10/2005 | Kodooka | |
| 6,953,461 B2 | 10/2005 | McClurken et al. | |
| 6,958,070 B2 | 10/2005 | Witt et al. | |
| 6,960,210 B2 | 11/2005 | Lands et al. | |
| 6,964,662 B2 | 11/2005 | Kidooka | |
| 6,966,907 B2 | 11/2005 | Goble | |
| 6,972,017 B2 | 12/2005 | Smith et al. | |
| 6,977,495 B2 | 12/2005 | Donofrio | |
| 6,979,786 B2 | 12/2005 | Aukland et al. | |
| 6,981,628 B2 | 1/2006 | Wales | |
| 6,987,244 B2 | 1/2006 | Bauer | |
| 6,994,707 B2 | 2/2006 | Ellman et al. | |
| 6,994,709 B2 | 2/2006 | Iida | |
| 6,997,931 B2 | 2/2006 | Sauer et al. | |
| 7,001,381 B2 | 2/2006 | Harano et al. | |
| 7,011,657 B2 | 3/2006 | Truckai et al. | |
| 7,033,354 B2 | 4/2006 | Keppel | |
| 7,033,356 B2 | 4/2006 | Latterell et al. | |
| 7,041,102 B2 | 5/2006 | Truckai et al. | |
| 7,044,948 B2 | 5/2006 | Keppel | |
| 7,052,489 B2 | 5/2006 | Griego et al. | |
| 7,052,496 B2 | 5/2006 | Yamauchi | |
| 7,063,715 B2 | 6/2006 | Onuki et al. | |
| D525,361 S | 7/2006 | Hushka | |
| 7,070,597 B2 | 7/2006 | Truckai et al. | |
| 7,083,618 B2 | 8/2006 | Couture et al. | |
| 7,083,619 B2 | 8/2006 | Truckai et al. | |
| 7,083,620 B2 | 8/2006 | Jahns et al. | |
| 7,087,051 B2 | 8/2006 | Bourne et al. | |
| 7,087,054 B2 | 8/2006 | Truckai et al. | |
| 7,090,673 B2 | 8/2006 | Dycus et al. | |
| 7,090,689 B2 | 8/2006 | Nagase et al. | |
| 7,101,371 B2 | 9/2006 | Dycus et al. | |
| 7,101,372 B2 | 9/2006 | Dycus et al. | |
| 7,101,373 B2 | 9/2006 | Dycus et al. | |
| 7,103,947 B2 | 9/2006 | Sartor et al. | |
| 7,107,124 B2 | 9/2006 | Green | |
| 7,112,199 B2 | 9/2006 | Cosmescu | |
| D531,311 S | 10/2006 | Guerra et al. | |
| 7,115,123 B2 | 10/2006 | Knowlton et al. | |
| 7,118,570 B2 | 10/2006 | Tetzlaff et al. | |
| 7,118,587 B2 | 10/2006 | Dycus et al. | |
| 7,131,860 B2 | 11/2006 | Sartor et al. | |
| 7,131,970 B2 | 11/2006 | Moses et al. | |
| 7,131,971 B2 | 11/2006 | Dycus et al. | |
| 7,135,020 B2 | 11/2006 | Lawes et al. | |
| D533,942 S | 12/2006 | Kerr et al. | |
| 7,145,757 B2 | 12/2006 | Shea et al. | |

| | | |
|---|---|---|
| 7,147,638 B2 | 12/2006 | Chapman et al. |
| 7,150,097 B2 | 12/2006 | Sremcich et al. |
| 7,150,749 B2 | 12/2006 | Dycus et al. |
| 7,153,314 B2 | 12/2006 | Laufer et al. |
| D535,027 S | 1/2007 | James et al. |
| 7,156,842 B2 | 1/2007 | Sartor et al. |
| 7,156,846 B2 | 1/2007 | Dycus et al. |
| 7,160,298 B2 | 1/2007 | Lawes et al. |
| 7,160,299 B2 | 1/2007 | Baily |
| 7,169,146 B2 | 1/2007 | Truckai et al. |
| 7,179,255 B2 | 2/2007 | Lettice et al. |
| 7,179,258 B2 | 2/2007 | Buysse et al. |
| 7,195,631 B2 | 3/2007 | Dumbauld |
| D541,418 S | 4/2007 | Schechter et al. |
| 7,207,990 B2 | 4/2007 | Lands et al. |
| D541,938 S | 5/2007 | Kerr et al |
| 7,223,264 B2 | 5/2007 | Daniel et al. |
| 7,223,265 B2 | 5/2007 | Keppel |
| 7,232,440 B2 | 6/2007 | Dumbauld et al. |
| 7,241,288 B2 | 7/2007 | Braun |
| 7,241,296 B2 | 7/2007 | Buysse et al. |
| 7,244,257 B2 | 7/2007 | Podhajsky et al. |
| 7,246,734 B2 | 7/2007 | Shelton, IV |
| 7,248,944 B2 | 7/2007 | Green |
| 7,252,667 B2 | 8/2007 | Moses et al. |
| 7,255,697 B2 | 8/2007 | Dycus et al. |
| 7,267,677 B2 | 9/2007 | Johnson et al. |
| 7,270,660 B2 | 9/2007 | Ryan |
| 7,270,664 B2 | 9/2007 | Johnson et al. |
| 7,276,068 B2 | 10/2007 | Johnson et al. |
| 7,300,435 B2 | 11/2007 | Wham et al. |
| 7,303,557 B2 | 12/2007 | Wham et al. |
| 7,311,709 B2 | 12/2007 | Truckai et al. |
| 7,314,471 B2 | 1/2008 | Holman |
| 7,318,823 B2 | 1/2008 | Sharps et al. |
| 7,329,256 B2 | 2/2008 | Johnson et al. |
| 7,329,257 B2 | 2/2008 | Kanehira et al. |
| D564,662 S | 3/2008 | Moses et al. |
| 7,338,526 B2 | 3/2008 | Steinberg |
| 7,342,754 B2 | 3/2008 | Fitzgerald et al. |
| 7,344,268 B2 | 3/2008 | Jigamian |
| D567,943 S | 4/2008 | Moses et al. |
| 7,367,976 B2 | 5/2008 | Lawes et al. |
| 7,377,920 B2 | 5/2008 | Buysse et al. |
| 7,384,420 B2 | 6/2008 | Dycus et al. |
| 7,384,421 B2 | 6/2008 | Hushka |
| 7,396,336 B2 | 7/2008 | Orszulak et al. |
| D575,395 S | 8/2008 | Hushka |
| D575,401 S | 8/2008 | Hixson et al. |
| 7,435,249 B2 | 10/2008 | Buysse et al. |
| 7,442,193 B2 | 10/2008 | Shields et al. |
| 7,442,194 B2 | 10/2008 | Dumbauld et al. |
| 7,445,621 B2 | 11/2008 | Dumbauld et al. |
| 7,458,972 B2 | 12/2008 | Keppel |
| 7,473,253 B2 | 1/2009 | Dycus et al. |
| 7,481,810 B2 | 1/2009 | Dumbauld et al. |
| 7,487,780 B2 | 2/2009 | Hooven |
| 7,491,201 B2 | 2/2009 | Shields et al. |
| 7,491,202 B2 | 2/2009 | Odom et al. |
| 7,500,975 B2 | 3/2009 | Cunningham et al. |
| 7,510,556 B2 | 3/2009 | Nguyen et al. |
| 7,513,898 B2 | 4/2009 | Johnson et al. |
| 7,540,872 B2 | 6/2009 | Schechter et al. |
| 7,549,995 B2 | 6/2009 | Schultz |
| 7,553,312 B2 | 6/2009 | Tetzlaff et al. |
| 2002/0013583 A1 | 1/2002 | Camran et al. |
| 2002/0049442 A1 | 4/2002 | Roberts et al. |
| 2002/0099372 A1 | 7/2002 | Schulze et al. |
| 2002/0107517 A1 | 8/2002 | Witt et al. |
| 2002/0111624 A1 | 8/2002 | Witt et al. |
| 2002/0188294 A1 | 12/2002 | Couture et al. |
| 2003/0014052 A1 | 1/2003 | Buysse et al. |
| 2003/0014053 A1 | 1/2003 | Nguyen et al. |
| 2003/0018331 A1 | 1/2003 | Dycus et al. |
| 2003/0018332 A1 | 1/2003 | Schmaltz et al. |
| 2003/0032956 A1 | 2/2003 | Lands et al. |
| 2003/0069570 A1 | 4/2003 | Witzel et al. |
| 2003/0069571 A1 | 4/2003 | Treat et al. |
| 2003/0078578 A1 | 4/2003 | Truckai et al. |
| 2003/0109875 A1 | 6/2003 | Tetzlaff et al. |
| 2003/0114851 A1 | 6/2003 | Truckai et al. |
| 2003/0139741 A1 | 7/2003 | Goble et al. |
| 2003/0139742 A1 | 7/2003 | Wampler et al. |
| 2003/0158548 A1 | 8/2003 | Phan et al. |
| 2003/0158549 A1 | 8/2003 | Swanson |
| 2003/0171747 A1 | 9/2003 | Kanehira et al. |
| 2003/0181910 A1 | 9/2003 | Dycus et al. |
| 2003/0216732 A1 | 11/2003 | Truckai et al. |
| 2003/0220637 A1 | 11/2003 | Truckai et al. |
| 2003/0229344 A1 | 12/2003 | Dycus et al. |
| 2003/0236325 A1 | 12/2003 | Bonora |
| 2003/0236518 A1 | 12/2003 | Marchitto et al. |
| 2004/0030330 A1 | 2/2004 | Brassell et al. |
| 2004/0030332 A1 | 2/2004 | Knowlton et al. |
| 2004/0049185 A1 | 3/2004 | Latterell et al. |
| 2004/0064151 A1 | 4/2004 | Mollenauer |
| 2004/0073238 A1 | 4/2004 | Makower |
| 2004/0073256 A1 | 4/2004 | Marchitto et al. |
| 2004/0078035 A1 | 4/2004 | Kanehira et al. |
| 2004/0082952 A1 | 4/2004 | Dycus et al. |
| 2004/0087943 A1 | 5/2004 | Dycus et al. |
| 2004/0115296 A1 | 6/2004 | Duffin |
| 2004/0116924 A1 | 6/2004 | Dycus et al. |
| 2004/0116979 A1 | 6/2004 | Truckai et al. |
| 2004/0122423 A1 | 6/2004 | Dycus et al. |
| 2004/0143263 A1 | 7/2004 | Schechter et al. |
| 2004/0148035 A1 | 7/2004 | Barrett et al. |
| 2004/0162557 A1 | 8/2004 | Tetzlaff et al. |
| 2004/0193153 A1 | 9/2004 | Sarter et al. |
| 2004/0199181 A1 | 10/2004 | Knodel et al. |
| 2004/0210282 A1 | 10/2004 | Flock et al. |
| 2004/0224590 A1 | 11/2004 | Rawa et al. |
| 2004/0230189 A1 | 11/2004 | Keppel |
| 2004/0236326 A1 | 11/2004 | Schulze et al. |
| 2004/0243125 A1 | 12/2004 | Dycus et al. |
| 2004/0249371 A1 | 12/2004 | Dycus et al. |
| 2004/0249374 A1 | 12/2004 | Tetzlaff et al. |
| 2004/0260281 A1 | 12/2004 | Baxter, III et al. |
| 2005/0004564 A1 | 1/2005 | Wham et al. |
| 2005/0004569 A1 | 1/2005 | Witt et al. |
| 2005/0021025 A1 | 1/2005 | Buysse et al. |
| 2005/0021027 A1 | 1/2005 | Shields et al. |
| 2005/0033278 A1 | 2/2005 | McClurken et al. |
| 2005/0059934 A1 | 3/2005 | Wenchell et al. |
| 2005/0096645 A1 | 5/2005 | Wellman et al. |
| 2005/0101951 A1 | 5/2005 | Wham et al. |
| 2005/0101952 A1 | 5/2005 | Lands et al. |
| 2005/0113818 A1 | 5/2005 | Sartor et al. |
| 2005/0113819 A1 | 5/2005 | Wham et al. |
| 2005/0113826 A1 | 5/2005 | Johnson et al. |
| 2005/0113828 A1 | 5/2005 | Shields et al. |
| 2005/0149017 A1 | 7/2005 | Dycus |
| 2005/0149151 A1 | 7/2005 | Orszulak et al. |
| 2005/0154387 A1 | 7/2005 | Moses et al. |
| 2005/0187547 A1 | 8/2005 | Sugi |
| 2005/0197659 A1 | 9/2005 | Bahney |
| 2005/0203504 A1 | 9/2005 | Wham et al. |
| 2005/0240179 A1 | 10/2005 | Buysse et al. |
| 2006/0052778 A1 | 3/2006 | Chapman et al. |
| 2006/0052779 A1 | 3/2006 | Hammill |
| 2006/0064085 A1 | 3/2006 | Schechter et al. |
| 2006/0064086 A1 | 3/2006 | Odom |
| 2006/0074417 A1 | 4/2006 | Cunningham et al. |
| 2006/0079888 A1 | 4/2006 | Mulier et al. |
| 2006/0079890 A1 | 4/2006 | Guerra |
| 2006/0079891 A1 | 4/2006 | Arts et al. |
| 2006/0079933 A1 | 4/2006 | Hushka et al. |
| 2006/0084973 A1 | 4/2006 | Hushka |
| 2006/0089670 A1 | 4/2006 | Hushka |
| 2006/0116675 A1 | 6/2006 | McClurken et al. |
| 2006/0129146 A1 | 6/2006 | Dycus et al. |
| 2006/0167450 A1 | 7/2006 | Johnson et al. |
| 2006/0167452 A1 | 7/2006 | Moses et al. |
| 2006/0173452 A1 | 8/2006 | Buysse et al. |
| 2006/0189980 A1 | 8/2006 | Johnson et al. |
| 2006/0189981 A1 | 8/2006 | Dycus et al. |
| 2006/0190035 A1 | 8/2006 | Hushka et al. |
| 2006/0217709 A1 | 9/2006 | Couture et al. |

| | | | |
|---|---|---|---|
| 2006/0224158 A1 | 10/2006 | Odom et al. | |
| 2006/0229666 A1 | 10/2006 | Suzuki et al. | |
| 2006/0253126 A1 | 11/2006 | Bjerken et al. | |
| 2006/0259036 A1 | 11/2006 | Tetzlaff et al. | |
| 2006/0264922 A1 | 11/2006 | Sartor et al. | |
| 2006/0264931 A1 | 11/2006 | Chapman et al. | |
| 2006/0283093 A1 | 12/2006 | Petrovic et al. | |
| 2006/0287641 A1 | 12/2006 | Perlin | |
| 2007/0016182 A1 | 1/2007 | Lipson et al. | |
| 2007/0016187 A1 | 1/2007 | Weinberg et al. | |
| 2007/0043352 A1 | 2/2007 | Garrison et al. | |
| 2007/0043353 A1 | 2/2007 | Dycus et al. | |
| 2007/0060919 A1 | 3/2007 | Isaacson et al. | |
| 2007/0062017 A1 | 3/2007 | Dycus et al. | |
| 2007/0074807 A1 | 4/2007 | Guerra | |
| 2007/0078456 A1 | 4/2007 | Dumbauld et al. | |
| 2007/0078458 A1 | 4/2007 | Dumbauld et al. | |
| 2007/0078459 A1 | 4/2007 | Johnson et al. | |
| 2007/0088356 A1 | 4/2007 | Moses et al. | |
| 2007/0106295 A1 | 5/2007 | Garrison et al. | |
| 2007/0106297 A1 | 5/2007 | Dumbauld et al. | |
| 2007/0118111 A1 | 5/2007 | Weinberg | |
| 2007/0118115 A1 | 5/2007 | Artale et al. | |
| 2007/0142833 A1 | 6/2007 | Dycus et al. | |
| 2007/0142834 A1 | 6/2007 | Dumbauld | |
| 2007/0156139 A1 | 7/2007 | Schechter et al. | |
| 2007/0156140 A1 | 7/2007 | Baily | |
| 2007/0173811 A1 | 7/2007 | Couture et al. | |
| 2007/0173814 A1 | 7/2007 | Hixson et al. | |
| 2007/0179499 A1 | 8/2007 | Garrison | |
| 2007/0198011 A1 | 8/2007 | Sugita | |
| 2007/0203485 A1 | 8/2007 | Keppel | |
| 2007/0213706 A1 | 9/2007 | Dumbauld et al. | |
| 2007/0213707 A1 | 9/2007 | Dumbauld et al. | |
| 2007/0213708 A1 | 9/2007 | Dumbauld et al. | |
| 2007/0213712 A1 | 9/2007 | Buysse et al. | |
| 2007/0255279 A1 | 11/2007 | Buysse et al. | |
| 2007/0260235 A1 | 11/2007 | Podhajsky | |
| 2007/0260238 A1 | 11/2007 | Guerra | |
| 2007/0260241 A1 | 11/2007 | Dalla Betta et al. | |
| 2007/0260242 A1 | 11/2007 | Dycus et al. | |
| 2007/0265616 A1 | 11/2007 | Couture et al. | |
| 2008/0004616 A1 | 1/2008 | Patrick | |
| 2008/0009860 A1 | 1/2008 | Odom | |
| 2008/0015575 A1 | 1/2008 | Odom et al. | |
| 2008/0021450 A1 | 1/2008 | Couture | |
| 2008/0033428 A1 | 2/2008 | Artale et al. | |
| 2008/0039835 A1 | 2/2008 | Johnson et al. | |
| 2008/0039836 A1 | 2/2008 | Odom et al. | |
| 2008/0045947 A1 | 2/2008 | Johnson et al. | |
| 2008/0058802 A1 | 3/2008 | Couture et al. | |
| 2008/0082100 A1 | 4/2008 | Orton et al. | |
| 2008/0091189 A1 | 4/2008 | Carlton | |
| 2008/0114356 A1 | 5/2008 | Johnson et al. | |
| 2008/0167651 A1 | 7/2008 | Tetzlaff et al. | |
| 2008/0195093 A1 | 8/2008 | Couture et al. | |
| 2008/0215051 A1 | 9/2008 | Buysse et al. | |
| 2008/0243120 A1 | 10/2008 | Lawes et al. | |
| 2008/0249527 A1 | 10/2008 | Couture | |
| 2008/0312653 A1 | 12/2008 | Arts et al. | |
| 2008/0319442 A1 | 12/2008 | Unger et al. | |
| 2009/0012520 A1 | 1/2009 | Hixson et al. | |
| 2009/0018535 A1 | 1/2009 | Schechter et al. | |
| 2009/0024126 A1 | 1/2009 | Artale et al. | |
| 2009/0043304 A1 | 2/2009 | Tetzlaff et al. | |
| 2009/0048596 A1 | 2/2009 | Shields et al. | |
| 2009/0062794 A1 | 3/2009 | Buysse et al. | |
| 2009/0082766 A1 | 3/2009 | Unger et al. | |
| 2009/0082767 A1 | 3/2009 | Unger et al. | |
| 2009/0082769 A1 | 3/2009 | Unger et al. | |
| 2009/0088738 A1 | 4/2009 | Guerra et al. | |
| 2009/0088739 A1 | 4/2009 | Hushka et al. | |
| 2009/0088740 A1 | 4/2009 | Guerra et al. | |
| 2009/0088741 A1 | 4/2009 | Hushka et al. | |
| 2009/0088744 A1 | 4/2009 | Townsend | |
| 2009/0088745 A1 | 4/2009 | Hushka et al. | |
| 2009/0088746 A1 | 4/2009 | Hushka et al. | |
| 2009/0088747 A1 | 4/2009 | Hushka et al. | |
| 2009/0088748 A1 | 4/2009 | Guerra et al. | |
| 2009/0088749 A1 | 4/2009 | Hushka et al. | |
| 2009/0088750 A1 | 4/2009 | Hushka et al. | |
| 2009/0112206 A1 | 4/2009 | Dumbauld et al. | |
| 2009/0131934 A1 | 5/2009 | Odom et al. | |
| 2009/0149853 A1 | 6/2009 | Shields et al. | |
| 2009/0149854 A1 | 6/2009 | Cunningham et al. | |
| 2009/0171350 A1 | 7/2009 | Dycus et al. | |
| 2009/0171353 A1 | 7/2009 | Johnson et al. | |
| 2009/0182327 A1 | 7/2009 | Unger | |
| 2009/0187188 A1 | 7/2009 | Guerra et al. | |

FOREIGN PATENT DOCUMENTS

| | | |
|---|---|---|
| DE | 2415263 | 10/1975 |
| DE | 2514501 | 10/1976 |
| DE | 2627679 | 1/1977 |
| DE | 3612646 | 4/1987 |
| DE | 8712328 | 3/1988 |
| DE | 4303882 | 8/1994 |
| DE | 4403252 | 8/1995 |
| DE | 195 15 914 C1 | 7/1996 |
| DE | 19515914 | 7/1996 |
| DE | 29616210 | 1/1997 |
| DE | 19608716 | 4/1997 |
| DE | 19751106 | 5/1998 |
| DE | 19751108 | 5/1999 |
| DE | 19738457 | 1/2009 |
| EP | 0364216 A1 | 4/1990 |
| EP | 0467501 | 1/1992 |
| EP | 0517243 | 12/1992 |
| EP | 0518230 A1 | 12/1992 |
| EP | 0541930 B1 | 5/1993 |
| EP | 0572131 | 12/1993 |
| EP | 0584787 A1 | 3/1994 |
| EP | 0589453 A2 | 3/1994 |
| EP | 0589555 | 3/1994 |
| EP | 0623316 A1 | 11/1994 |
| EP | 0624348 A2 | 11/1994 |
| EP | 0650701 A1 | 5/1995 |
| EP | 0694290 A3 | 3/1996 |
| EP | 0717966 A1 | 6/1996 |
| EP | 0754437 A3 | 3/1997 |
| EP | 0517243 | 9/1997 |
| EP | 0853922 A1 | 7/1998 |
| EP | 0875209 A1 | 11/1998 |
| EP | 0878169 A1 | 11/1998 |
| EP | 0887046 A3 | 1/1999 |
| EP | 0923907 A1 | 6/1999 |
| EP | 0986990 A1 | 3/2000 |
| EP | 1034747 A1 | 9/2000 |
| EP | 1034748 A1 | 9/2000 |
| EP | 1025807 A3 | 10/2000 |
| EP | 1034746 A3 | 10/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1080694 A1 | 3/2001 |
| EP | 1082944 A1 | 3/2001 |
| EP | 1159926 A2 | 12/2001 |
| EP | 1177771 | 2/2002 |
| EP | 1301135 A | 4/2003 |
| EP | 1330991 A1 | 7/2003 |
| EP | 1486177 A2 | 6/2004 |
| EP | 1472984 A1 | 11/2004 |
| EP | 0774232 | 1/2005 |
| EP | 1527747 A2 | 5/2005 |
| EP | 1530952 A1 | 5/2005 |
| EP | 1532932 A1 | 5/2005 |
| EP | 1535581 A2 | 6/2005 |
| EP | 1609430 A1 | 12/2005 |
| EP | 1632192 A1 | 3/2006 |
| EP | 1642543 | 4/2006 |
| EP | 1645238 A1 | 4/2006 |
| EP | 1645240 A2 | 4/2006 |
| EP | 1649821 | 4/2006 |
| EP | 1707143 A1 | 10/2006 |
| EP | 1769765 | 4/2007 |
| EP | 1769766 | 4/2007 |

| | | |
|---|---|---|
| EP | 1929970 | 6/2008 |
| EP | 1683496 | 12/2008 |
| GB | 623316 | 5/1949 |
| GB | 1490585 | 11/1977 |
| GB | 2214430 A | 6/1989 |
| GB | 2213416 | 8/1989 |
| JP | 501068 | 9/1984 |
| JP | 502328 | 3/1992 |
| JP | 5-5106 | 1/1993 |
| JP | 5-40112 | 2/1993 |
| JP | 06343644 A2 | 12/1994 |
| JP | 07265328 A2 | 10/1995 |
| JP | 08056955 A2 | 3/1996 |
| JP | 08252263 A2 | 10/1996 |
| JP | 09010223 A2 | 1/1997 |
| JP | 11244298 A2 | 9/1999 |
| JP | 2000342599 A2 | 12/2000 |
| JP | 2000350732 A2 | 12/2000 |
| JP | 2001008944 A2 | 1/2001 |
| JP | 2001029356 A2 | 2/2001 |
| JP | 2001128990 A2 | 5/2001 |
| SU | 401367 | 11/1974 |
| WO | WO 89/00757 | 1/1989 |
| WO | WO 92/04873 | 4/1992 |
| WO | WO 92/06642 | 4/1992 |
| WO | WO 93/21845 | 11/1993 |
| WO | WO 94/08524 A | 4/1994 |
| WO | WO 94/20025 | 9/1994 |
| WO | WO 95/02369 | 1/1995 |
| WO | WO 95/07662 | 3/1995 |
| WO | WO 95/15124 | 6/1995 |
| WO | WO 96/05776 | 2/1996 |
| WO | WO 96/22056 | 7/1996 |
| WO | WO 96/13218 | 9/1996 |
| WO | WO 97/00646 | 1/1997 |
| WO | WO 97/00647 | 1/1997 |
| WO | WO 97/10764 | 3/1997 |
| WO | WO 97/24073 | 7/1997 |
| WO | WO 97/24993 | 7/1997 |
| WO | WO 98/27880 | 7/1998 |
| WO | WO 99/03407 | 1/1999 |
| WO | WO 99/03408 | 1/1999 |
| WO | WO 99/03409 | 1/1999 |
| WO | WO 99/12488 | 3/1999 |
| WO | WO 99/23933 | 5/1999 |
| WO | WO 99/40857 | 8/1999 |
| WO | WO 99/40861 | 8/1999 |
| WO | WO 99/51158 | 10/1999 |
| WO | WO 99/66850 A | 12/1999 |
| WO | WO 00/24330 | 5/2000 |
| WO | WO 00/24331 | 5/2000 |
| WO | WO 00/36986 | 6/2000 |
| WO | WO 00/41638 | 7/2000 |
| WO | WO 00/47124 | 8/2000 |
| WO | WO 00/53112 | 9/2000 |
| WO | WO 01/17448 A | 3/2001 |
| WO | WO 01/54604 | 8/2001 |
| WO | WO 02/07627 | 1/2002 |
| WO | WO 02/067798 A1 | 9/2002 |
| WO | WO 02/080783 | 10/2002 |
| WO | WO 02/080784 | 10/2002 |
| WO | WO 02/080785 | 10/2002 |
| WO | WO 02/080786 | 10/2002 |
| WO | WO 02/080793 | 10/2002 |
| WO | WO 02/080794 | 10/2002 |
| WO | WO 02/080795 | 10/2002 |
| WO | WO 02/080796 | 10/2002 |
| WO | WO 02/080797 | 10/2002 |
| WO | WO 02/080798 | 10/2002 |
| WO | WO 02/080799 | 10/2002 |
| WO | WO 02/081170 | 10/2002 |
| WO | WO 03/061500 | 7/2003 |
| WO | WO 03/090630 A3 | 11/2003 |
| WO | WO 03/101311 | 12/2003 |
| WO | WO 2004/032776 A1 | 4/2004 |
| WO | WO 2004/032777 | 4/2004 |
| WO | WO 2004/052221 | 6/2004 |
| WO | WO 2004/073488 A2 | 9/2004 |
| WO | WO 2004/073490 | 9/2004 |
| WO | WO 2004/073753 | 9/2004 |
| WO | WO 2004/082495 | 9/2004 |
| WO | WO 2004/098383 | 11/2004 |
| WO | WO 2004/103156 | 12/2004 |
| WO | 2005/004734 A1 | 1/2005 |
| WO | WO 2005/004735 | 1/2005 |
| WO | WO 2005/110264 | 11/2005 |
| WO | WO 2008/045348 | 4/2008 |
| WO | WO 2008/045350 | 4/2008 |

OTHER PUBLICATIONS

European Examination Report mailed Dec. 22, 2009 in a counterpart European Application No. 08020807.7.
Int'l Search Report EP 06 020574.7 dated Sep. 21, 2007.
Int'l Search Report EP 07 010672.9 dated Oct. 1, 2007.
Int'l Search Report EP 07 013779.9 dated Oct. 18, 2007.
Int'l Search Report EP 07 009026.1 dated Sep. 12, 2007.
Int'l Search Report EP 07 015601.3 dated Dec. 6, 2007.
Int'l Search Report EP 07 015191.5 dated Dec. 19, 2007.
Int'l Search Report EP 07 020283.3 dated Jan. 16, 2008.
International Search Report EP 05019429.9 dated May 6, 2008.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Crouch et al. "A Velocity-Dependent Model for Needle Insertion in Soft Tissue" MICCAI 2005; LNCS 3750 pp. 624-632, Dated: 2005.
Int'l Search Report EP 98957771 dated Aug. 9, 2001.
Int'l Search Report EP 05002671.5 dated Dec. 22, 2008.
Int'l Search Report EP 05002674.9 dated Jan. 16, 2009.
Int'l Search Report EP 05019429.9 dated May 6, 2008.
Int'l Search Report EP 06008515.6 dated Jan. 8, 2009.
Int'l Search Report EP 07 014016 dated Jan. 28, 2008.
Int'l Search Report EP 07 021646.0 dated Jul. 9, 2008.
Int'l Search Report EP 07 021647.8 dated May 2, 2008.
Int'l Search Report EP 08 02692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 152267.2 Dated Jun. 15, 2009.
Int'l Search Report EP 09 152898.4 Dated Jun. 10, 2009.
Int'l Search Report PCT/US98/24281 dated Feb. 22, 1999.
Int'l Search Report PCT/US03/28534 dated Dec. 19, 2003.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report PCT/US09/032690 dated Jun. 16, 2009.
Sigel et al. "The Mechanism of Blood Vessel Closure by High Frequency Electrocoagulation" Surgery Gynecology & Obstetrics, Oct. 1965 pp. 823-831.
Bergdahl et al. "Studies on Coagulation and the Development of an Automatic Computerized Bipolar Coagulator" J.Neurosurg, vol. 75, Jul. 1991, pp. 148-151.
Kennedy et al. "High-burst-strength, feedback-controlled bipolar vessel sealing" Surgical Endoscopy (1998) 12: 876-878.
Peterson et al. "Comparison of Healing Process Following Ligation with Sutures and Bipolar Vessel Sealing" Surgical Technology International (2001).
Linehan et al. "A Phase I Study of the LigaSure Vessel Sealing System in Hepatic Surgery" Section of HPB Surger, Washington University School of Medicine, St. Louis MO, Presented at AHPBA, Feb. 2001.
Johnson at al. "Evaluation of the LigaSure Vessel Sealing System in Hemorrhoidectormy" American College of Surgeons (ACS) Clinicla Congress Poster (2000).
Sayfan et al. "Sutureless Closed Hemorrhoidectomy: A New Technique" Annals of Surgery vol. 234 No. 1 Jul. 2001 pp. 21-24.
Heniford et al. "Initial Results with an Electrothermal Bipolar Vessel Sealer" Surgical Endoscopy (2000) 15:799-801.
Heniford at al. "Initial Research and Clinical Results with an Electrothermal Bipolar Vessel Sealer" Oct. 1999.

McLellan et al. "Vessel Sealing for Hemostasis During Pelvic Surgery" Int'l Federation of Gynecology and Obstetrics FIGO World Congress 2000, Washington, D.C.

Levy et al. "Use of a New Energy-based Vessel Ligation Device During Vaginal Hysterectomy" Int'l Federation of Gynecology and Obstetrics (FIGO) World Congress 1999.

Crawford et al. "Use of the LigaSure Vessel Sealing System in Urologic Cancer Surger" Grand Rounds in Urology 1999 vol. 1 Issue 4 pp. 10-17.

Rothenberg at al. "Use of the LigaSure Vessel Sealing System in Minimally Invasive Surgery in Children" Int'l Pediatric Endosurgery Group (IPEG) 2000.

Palazzo et al. "Randomized clinical trial of Ligasure versus open haemorrhoidectomy" British Journal of Surgery 2002, 89, 154-157.

"Innovations in Electrosurgery" Sales/Product Literature; Dec. 31, 2000.

LigaSure Vessel Sealing System, the Seal of Confidence in General, Gynecologic, Urologic, and Laparaoscopic Surgery Sales/Product Literature; Jan. 2004.

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC 2003.

"Reducing Needlestick Injuries in the Operating Room" Sales/Product Literature 2001.

Chung at al.. "Clinical Experience of Sutureless Closed Hemorrhoidectomy with LigaSure" Diseases of the Colon & Rectum vol. 48, No. 1 Jan. 2003.

Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.

Paul G. Horgan, "A Novel Technique for Parenchymal Division During Hepatectomy" The American Journal of Surgery, vol. 181, No. 3, Apr. 2001 pp. 236-237.

W. Scott Helton, "LigaSure Vessel Sealing System: Revolutionary Hemostasis Product for General Surgery" Sales/Product Literature 1999.

Michael Choti, "Abdominoperineal Resection with the LigaSure Vessel Sealing System and LigaSure Atlas 20 cm Open Instrument" Innovations That Work, Jun. 2003.

Craig Johnson, "Use of the LigaSure Vessel Sealing System in Bloodless Hemorrhoidectomy" Innovations That Work, Mar. 2000.

Muller et al., "Extended Left Hemicolectomy Using the LigaSure Vessel Sealing System" Innovations That Work, Sep. 1999.

Herman et al., "Laparoscopic Intestinal Resection With the LigaSure Vessel Sealing System: A Case Report" Innovations That Work, Feb. 2002.

Carus et al., "Initial Experience With the LigaSure Vessel Sealing System in Abdominal Surgery" Innovations That Work, Jun. 2002.

Levy et al. "Randomized Trial of Suture Versus Electrosurgical Bipolar Vessel Sealing in Vaginal Hysterectomy" Obstetrics & Gynecology, vol. 102, No. 1, Jul. 2003.

Levy et al., "Update on Hysterectomy—New Technologies and Techniques" OBG Management, Feb. 2003.

Barbara Levy, "Use of a New Vessel Ligation Device During Vaginal Hysterectomy" FIGO 2000, Washington, D.C.

McLellan et el. "Vessel Sealing for Hemostasis During Gynecologic Surgery" Sales/Product Literature 1999.

Sengupta et al., "Use of a Computer-Controlled Bipolar Diathermy System in Radical Prostatectomies and Other Open Urological Surgery" ANZ Journal of Surgery (2001) 71.9 pp. 538-540.

Olsson at al. "Radical Cystectomy in Females" Current Surgical Techniques in Urology, vol. 14, Issue 3. 2001.

E. David Crawford "Use of a Novel Vessel Sealing Technology in Management of the Dorsal Veinous Complex" Sales/Product Literature 2000.

Jarrett et al., "Use of the LigaSure Vessel Sealing System for Peri-Hilar Vessels in Laparoscopic Nephrectomy" Sales/Product Literature 2000.

E. David Crawford "Evaluation of a New Vessel Sealing Device in Urologic Cancer Surgery" Sales/Product Literature 2000.

Joseph Ortenberg "LigaSure System Used in Laparoscopic 1st and 2nd Stage Orchiopexy" Innovations That Work, Nov. 2002.

Koyle at al., "Laparoscopic Patomo Varicocele Ligation in Children and Adolescents" Pediatric Endosurgery & Innovative Techniques, vol. 6. No. 1, 2002.

Dulemba et al. "Use of a Bipolar Electrothermal Vessel Sealer in Laparoscopically Assisted Vaginal Hysterectomy" Sales/Product Literature; Jan. 2004.

Johnson et al. "Evaluation of a Bipolar electrothermal Vessel Sealing Device in Hemorrhoidectomy" Sales/Product Literature; Jan. 2004.

Int'l Search Report PCT/US98/18640 dated Dec. 17, 1998.
Int'l Search Report PCT/US98/23950 dated Dec. 29, 1998.
Int'l Search Report PCT/US99/24869 dated Feb. 3, 2000.
Int'l Search Report PCT/US01/11218 dated Aug. 3, 2001.
International Search Report PCT/US01/11224 dated Nov. 13, 2001.
Int'l Search Report PCT/US01/11340 dated Aug. 7, 2001.
Int'l Search Report PCT/US01/11420 dated Oct. 8, 2001.
Int'l Search Report PCT/US02/01890 dated Jul. 17, 2002.
Int'l Search Report PCT/US02/11100 dated Jul. 9, 2002.
Int'l Search Report PCT/US04/03436 dated Oct. 5, 2004.
Int'l Search Report PCT/US04/13273 dated Nov. 22, 2004.
Int'l Search Report PCT/US04/15311 dated Nov. 18, 2004.
Int'l Search Report EP 98944778 dated Oct. 31, 2000.
Int'l Search Report EP 98958575.7 dated Sep. 20, 2002.
Int'l Search Report EP 04027314 dated Mar. 10, 2005.
Int'l Search Report EP 04027479 dated Mar. 8, 2005.
Int'l Search Report EP 04027705 dated Feb. 3, 2005.
Int'l Search Report EP 04013772 dated Apr. 1, 2005.
Int'l Search Report EP 05013463.4 dated Sep. 28, 2005.
Int'l Search Report EP 05013895 dated Oct. 14, 2005.
Int'l Search Report EP 05016399 dated Jan. 5, 2006.
Int'l Search Report EP 05017281 dated Nov. 16, 2005.
Int'l Search Report EP 05019130.3 dated Oct. 18, 2005.
Int'l Search Report EP 05020665.5 dated Feb. 16, 2006.
Int'l Search Report EP 05020666.3 dated Feb. 17, 2006.
Int'l Search Report EP 05021779.3 dated Jan. 18, 2006.
Int'l Search Report EP 05021197.8 dated Jan. 31, 2006.
Int'l Search Report EP 05021937.7 dated Jan. 13, 2006.
Int'l Search Report—extended—EP 05021937.7 dated Mar. 6, 2006.
Int'l Search Report EP 05023017.6 dated Feb. 16, 2006.
Int'l Search Report EP 05021780.1 dated Feb. 9, 2006.
Int'l Search Report EP 06002279.5 dated Mar. 22, 2006.
Int'l Search Report EP 06005185.1 dated Apr. 18, 2006.
Int'l Search Report EP 06006716 dated Aug. 4, 2006.
Int'l Search Report EP 06008779.8 dated Jun. 13, 2006.
Int'l Search Report EP 1683496 dated Jun. 13, 2006.
Int'l Search Report EP 06014461.5 dated Oct. 20, 2006.
Int'l Search Report EP 06020584.6 dated Jan. 12, 2007.
Int'l Search Report EP 06020583.8 dated Jan. 30, 2007.
Int'l Search Report EP 06020756.0 dated Feb. 5, 2007.
Int'l Search Report EP 06024123.9 dated Feb. 26, 2007.
Int'l Search Report EP 04 752343.6 dated Jul. 20, 2007.
Int'l Search Report EP 06 024122.1 dated Mar. 19, 2007.
Int'l Search Report EP 07 001480.8 dated Apr. 12, 2007.
Int'l Search Report EP 07 001488.1 dated May 29, 2007.
Int'l Search Report Extended—EP 07 009029.5 dated Jul. 12, 2007.
Int'l Search Report EP 07 009321.6 dated Aug. 17, 2007.

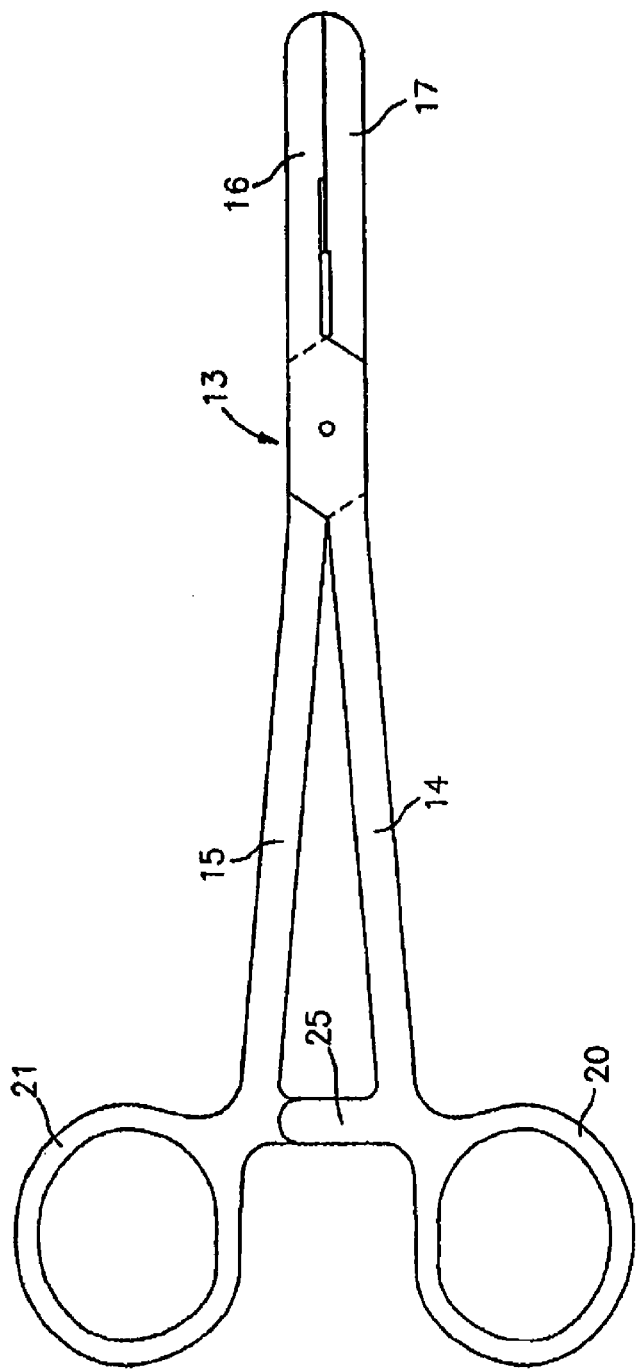
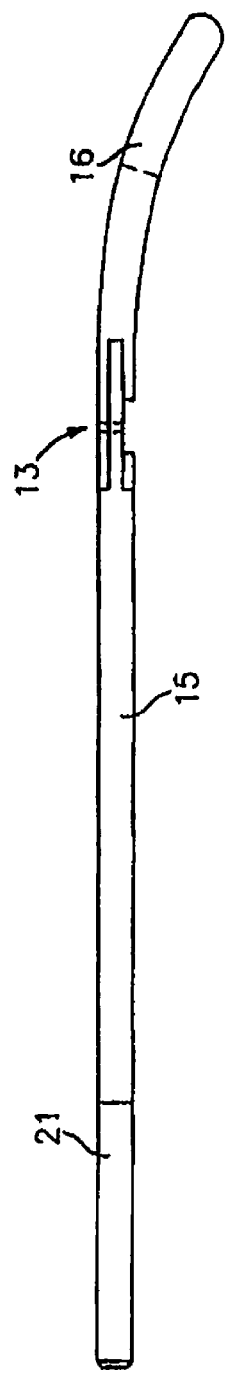
FIG. 4
FIG. 5

BIPOLAR ELECTROSURGICAL INSTRUMENT FOR SEALING VESSELS

CROSS REFERENCE TO RELATED APPLICATIONS

This application is a continuation of U.S. application Ser. No. 10/736,180 filed on Dec. 15, 2003 by Buysse et al. entitled "BIPOLAR ELECTROSURGICAL INSTRUMENT FOR SEALING VESSELS" now U.S. Pat No. 7,241,296 which is a continuation of U.S. application Ser. No. 10/113,745 filed on Apr. 1, 2002 by Buysse et al. entitled "BIPOLAR ELECTROSURGICAL INSTRUMENT FOR SEALING VESSELS", now U.S. Pat. No. 6,726,686, which is a continuation-in-part of U.S. application Ser. No. 10/090,081 filed on Mar. 1, 2002 by Buysse et al. entitled "BIPOLAR ELECTROSURGICAL INSTRUMENT FOR SEALING VESSELS", now U.S. Pat. No. 6,743,229, which is a continuation of U.S. application Ser. No. 09/502,933 filed on Feb. 11, 2000 by Buysse et al. entitled "BIPOLAR ELECTROSURGICAL INSTRUMENT FOR SEALING VESSELS", now U.S. Pat. No. 6,352,536, which is a continuation of U.S. application Ser. No. 08/968,779 filed on Nov. 12, 1997 by Buysse et al. entitled "BIPOLAR ELECTROSURGICAL INSTRUMENT FOR SEALING VESSELS", now U.S. Pat. No. 6,187,003, the entire contents of all of these applications are incorporated herein by reference in their entirety.

BACKGROUND

1. Field of the Invention

This invention relates to an electrosurgical instrument for permanently closing vessels in a human or animal, and more particularly to a bipolar electrosurgical instrument that seals vessels and vascular tissue by applying a combination of pressure and electrosurgical current.

2. Background of Related Art

A hemostat is commonly used in surgical procedures to grasp, dissect and clamp tissue. It is typically a simple pliers-like tool that uses mechanical action between its jaws to constrict vessels without cutting them. It is also typical for hemostats to have an interlocking ratchet between the handles so that the device can be clamped and locked in place.

Many hemostats are used in a typical open-surgical procedure. Once vascular tissue has been clamped with a hemostat, it is common for a surgeon to tie a suture around the tissue to close it off permanently prior to removing the hemostat. Several hemostats may be left in the surgical field until the surgeon has the opportunity to tie a suture around each section of clamped tissue.

Small blood vessels have been closed using electrosurgical instruments without the need for sutures. For example, neurosurgeons have used bipolar instruments to coagulate vessels in the brain that are smaller than two millimeters in diameter. These bipolar instruments are typically tweezers-like devices with two arms that can be deflected toward each other to grasp tissue. However, it has been found that these instruments are not capable of sealing blood vessels with diameters larger than about two millimeters. There has been a long-felt need for an easy way to seal larger vessels and vascular tissue bundles without the need for sutures.

It is thought that the process of coagulating small vessels is fundamentally different than vessel sealing. Coagulation is defined as a process of desiccating tissue wherein the tissue cells are ruptured and dried. Vessel sealing is defined as the process of liquefying the collagen in the tissue so that it crosslinks and reforms into a fused mass. Thus, coagulation of small vessels is sufficient to permanently close them. Larger vessels need to be sealed to assure permanent closure.

A number of bipolar electrosurgical forceps and clamps are known in the field. However, these instruments are not designed to apply the correct pressure to a blood vessel to achieve a lasting seal. All of these instruments also suffer from the drawback that they do not combine the simplicity and familiarity of a hemostat with a bipolar electrosurgical circuit.

An example of a bipolar electrosurgical power curve for vessel sealing is disclosed in a U.S. patent application entitled, "Energy Delivery System for Vessel Sealing," Ser. No. 08/530,495, filed Sep. 19, 1995, and is hereby incorporated by reference and made a part of this disclosure.

A U.S. patent application entitled, "Vascular Tissue Sealing Pressure Control and Method," Ser. No. 08/530,450, filed on Sep. 19, 1995, discloses another surgical tool for sealing vessels, and is hereby incorporated by reference and made a part of this disclosure.

U.S. Pat. No. 371,664 discloses a pair of electric forceps with positive and negative electric poles located on the jaws.

U.S. Pat. No. 728,883 discloses an electrothermic instrument in which electricity is used to heat one of the jaws of the instrument.

U.S. Pat. No. 1,586,645 discloses a bipolar instrument for coagulating tissue.

U.S. Pat. No. 2,002,594 discloses a bipolar laparoscopic instrument for treating tissue, whereby coagulation and cutting of tissue can be performed with the same instrument.

U.S. Pat. No. 2,176,479 discloses an instrument for finding and removing metal particles. The jaws of the instrument are designed to complete an electrical circuit when conductive material is placed therebetween. An insulated pivot and an insulated ratchet are used to prevent a short circuit.

U.S. Pat. No. 3,651,811 discloses a bipolar electrosurgical instrument for cutting and coagulating tissue.

U.S. Pat. No. 4,005,714 discloses bipolar coagulation forceps with jaws that open and close by way of an actuating sleeve.

U.S. Pat. Nos. 4,370,980 and 5,116,332 disclose an electrocautery hemostats wherein the hemostatic clamping function and the electrocautery function may be accomplished with a single instrument. Monopolar electrosurgical designs are shown and described.

U.S. Pat. No. 4,552,143 discloses a family of removable switch electrocautery instruments, including an electrocautery hemostat. Monopolar electrosurgical designs are shown and described.

U.S. Pat. No. 5,026,370 discloses an electrocautery forceps instrument having an enclosed electrical switching mechanism. Monopolar electrosurgical designs are shown and described.

U.S. Pat. No. 5,443,463 discloses coagulating forceps having a plurality of electrodes.

U.S. Pat. No. 5,484,436 discloses bipolar electrosurgical instruments for simultaneously cutting and coagulating tissue.

The article, "The Mechanism of Blood Vessel Closure by High Frequency Electrocoagulation" discloses experiments upon the blood vessels of dogs. The sentence starting on the last line of page 823 describes "an electrode forceps, each of the blades being insulated form the other and each connected to a terminal of the high frequency generator."

The article, "Studies on coagulation and development of an automatic computerized bipolar coagulator" discloses on page 150 that, "It was not possible to coagulate safely arteries with a diameter larger than 2 to 2.5 mm." On page 151, line 5, it is noted that "Veins can be coagulated safely up to a diameter of 3 to 4 mm."

Russian Patent 401,367 discloses a bipolar instrument with a linkage that brings the working jaws together in a parallel manner.

Prior disclosures have not provided a design for a bipolar electrosurgical instrument capable of conveniently applying a constant pressure, from a calibrated spring-loaded source held by a ratchet, that is sufficient to seal vessels and vascular tissue.

SUMMARY OF THE INVENTION

It is the general objective of this invention to provide a bipolar electrosurgical instrument that can fuse tissue without the need for a suture or surgical clips. The instrument conducts electrosurgical current between two seal surfaces located on opposable jaws. The electrosurgical current passes through tissue clamped between the jaws and remolds the collagen to fuse the tissue and form a permanent seal.

One advantage of the invention is that blood vessels can be quickly fused and permanently sealed against passage of blood or other fluids. The instrument thereby reduces operating-room time, provides improved access to target tissues, and increases the efficiency of the surgical procedure.

Another advantage is that no sutures or staples are required to permanently seal blood vessels, and no foreign material is left in the body of the patient.

Yet another advantage is that vessels can be sealed as the instrument is applied, and then the instrument can be removed from the surgical field. This keeps the surgical field clear of extraneous tools that may hinder the surgeon's access to the surgical site.

Yet another advantage is that the proper amount of pressure can be applied by the instrument to the vessel or vessels, thereby increasing the likelihood of a successful surgical outcome.

The bipolar electrosurgical instrument of the present invention comprises inner and outer members connected by an open lockbox, interlocking ratchet teeth, and electrical terminals with conductive pathways leading to seal surfaces. The inner and outer members each have a ring handle near a proximal end and an opposable seal surface near a distal end. The proximal end is held and controlled by the surgeon, while the distal end is used to manipulate tissue. The open lockbox joins the inner and outer members to allow arcuate motion of each opposable seal surface. The open lockbox is generally designed to provide lateral support so that both seal surfaces move in approximately the same plane. The seal surfaces are preferably aligned opposite each other when the instrument jaws are closed together. To provide lateral support, the open lockbox comprises a pivot and at least one flange extending over the inner member and attached to the outer member.

The instrument is tuned to provide a proper closure force by adjusting the dimensions of a shank portion on each of the inner and outer members. The shank portion is defined as the portion of each member bounded by its respective ratchet stub and the open lockbox. During use, the surgeon squeezes the ring handles to compress tissue between the seal surfaces. The shank portion of each member flexes in the manner of a cantilever spring, and can be locked in a deflected position with the ratchet to hold a constant force. It is one of the objects of the invention to provide a range of ratchet stops that correspond to a range of appropriate closure forces on the seal surfaces of the instrument.

Ratchet teeth are located on each member near the ring handle. The ratchet teeth are generally designed to interlock against the spring force from the shanks. The spring force is thus transmitted through the pivot to hold the seal surfaces against each other. A range of closure forces is required in an instrument, depending on the type and thickness of the tissue to be sealed. It is thus desirable to have several ratchet stops, each providing a progressively larger force to the seal surfaces.

An electrical connector is located on each ring handle. The electrical connector may be a metal post that is integrally formed with the member and ring handle. Bipolar electrical cables from an electrosurgical generator are connected to the instrument at the electrical connectors. An electrically conductive path on each of the inner and outer members conducts the electrosurgical current to the seal surfaces. The electrically conductive path may be along the stainless steel members. An electrically insulative coating is preferably bonded to the outer surfaces of the members to protect the surgeon and patient against inadvertent electrical burns.

The following terms are herein defined as follows. The applied force of the instrument is the total force being applied to the tissue between the jaws. The jaws are the members near the distal end of the instrument, from the lockbox to the tip of the instrument. The electrodes are the metal surfaces that conduct electricity to the tissue. The seal surface is the feature on the electrode that comes in direct contact with the tissue. The shank is the portion of each member between the lockbox and the ratchet. The ring handles are the elements on the members, near the proximal end of the instrument, that are grasped by the surgeon. The lockbox is the structure that allows the members to pivot, including the pivot pin and other cooperating surfaces. The inner member is the member that is generally captured in the interior of the lockbox. The outer member is the member that is on the outside of the lockbox. Electrode pressure is calculated by dividing the applied force over the complete area of the seal surface. Tissue pressure is calculated by dividing the applied force over the area of tissue placed between the jaws.

It has been found through experimentation that an instrument for vessel fusion (also referred herein as vessel sealing) should compress the tissue with a proper amount of pressure between the instrument jaws. The pressure is preferably sufficient to close any blood-carrying lumen. The pressure is preferably low enough so that the tissue is not split apart within the instrument jaws.

The jaws of the instrument should not short-circuit during the procedure. The tissue will typically decrease in thickness when electrosurgical current is applied, thereby allowing the seal surfaces to move closer together. This decrease in thickness should not result in the electrodes making direct contact with each other. Otherwise, a short circuit could give the electrosurgical current a preferential path around the tissue and may result in a poor seal.

BRIEF DESCRIPTION OF THE DRAWINGS

FIG. 4 is a schematic plan view of an alternative embodiment of an instrument for vessel fusion having a shorter curved jaw.

FIG. 5 is side view of the instrument shown in FIG. 4.

DETAILED DESCRIPTION OF THE INVENTION

Figure 1:
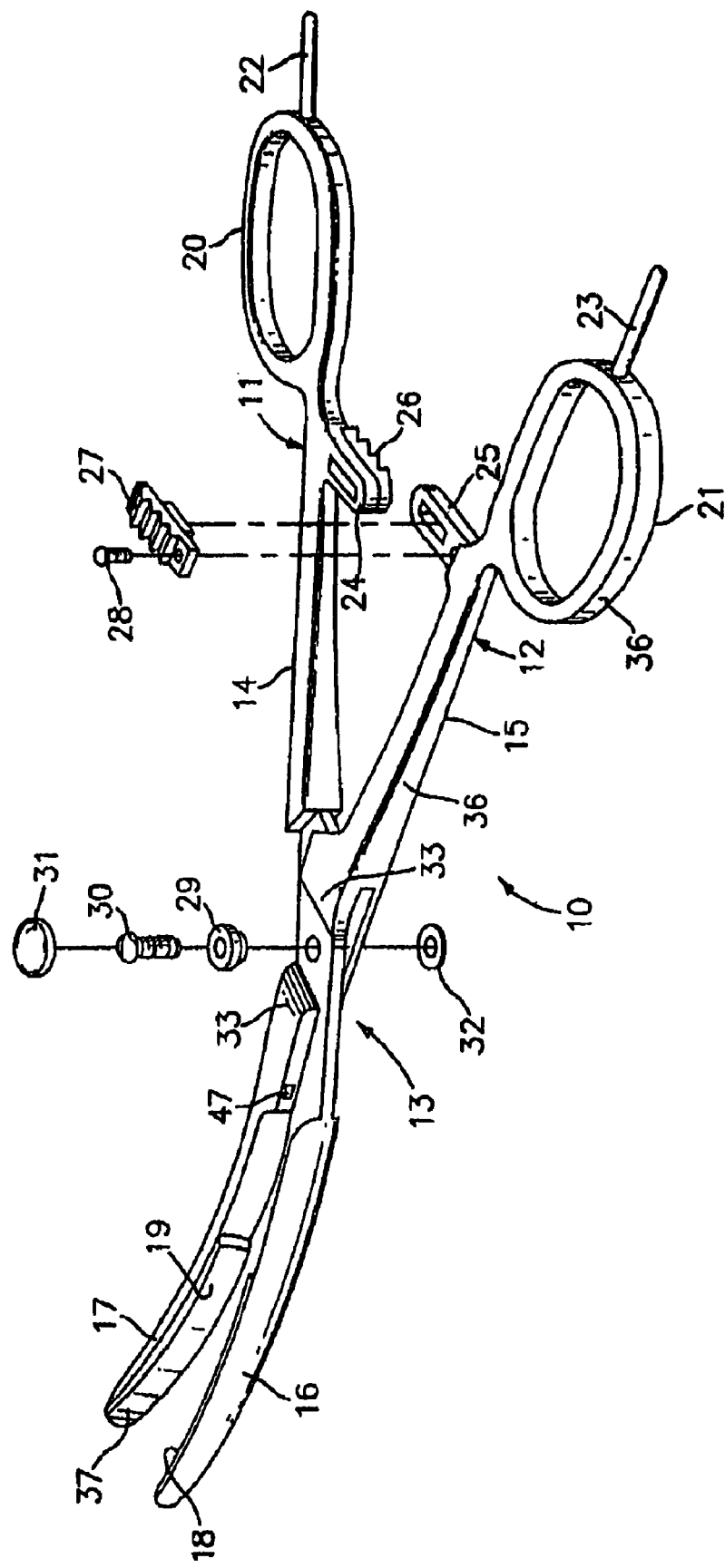
FIG. 1 is a perspective view of a bipolar instrument for vessel fusion, shown partially exploded.

Referring to FIG. 1, the instrument 10 has an inner member 11 and an outer member 12. The members 11 and 12 are connected through an open lockbox 13 which has a gap between flanges 33. The terms "inner" and "outer" are used to distinguish the members 11 and 12, and their component parts, according to the members' respective positions at the open lockbox 13. The inner member 11 is fitted generally within the inner surfaces of the open lockbox 13 and is captured by the flanges 33. The outer member generally forms the outside surfaces of the open lockbox 13.

The inner member 11 has an inner shank 14, an inner jaw 16, and an inner ring handle 20. Similarly, the outer member 12 has an outer shank 15, an outer jaw 17, and an outer ring handle 21. The ring handles, 20 and 21, are designed for a surgeon to hold and manipulate the instrument 10. The jaws, 16 and 17, are designed to grasp tissue between the opposing seal surfaces 18 and 19.

Each shank, 14 and 15, has a respective ratchet stub 24 or 25. Ratchet teeth, 26 and 27, are designed to interlock in a manner that hold the members, 11 and 12, in position. The shanks 14 and 15 are deflected in the manner of a cantilever spring when the jaws are forced together by the surgeon. The deflection of the shanks 14 and 15 produces a spring restoring force that can be opposed by interlocking the ratchet teeth, 26 and 27.

The instrument 10 does not cause a short circuit when the ratchet teeth, 26 and 27, are interlocked. This is accomplished by a suitable selection and placement of electrically insulating materials. In the preferred embodiment, the ratchet teeth 26 and 27 are composed of a polymeric material which is press-fit into the ratchet stubs 24 and 25. A ratchet screw 28 is used in the preferred embodiment to secure the ratchet teeth 26 and 27 into the ratchet stubs 24 and 25. During manufacture, the ratchet teeth 26 and 27 may be formed from a blank after the blank has been press fit into the ratchet stubs 24 and 25.

In a second embodiment, one of the members, 11 or 12, includes the ratchet stub and ratchet teeth as in integral part of the member, while the other member, 12 or 11, has an insulative layer that prevents a short circuit between the members 11 and 12 when the ratchets are engaged.

The open lockbox 13 has the function of providing a pivoting joint for the members 11 and 12. In addition, the flanges 33 provide lateral support to help maintain alignment of the jaws 16 and 17. Closed lockbox designs are typically used in standard hemostat designs, wherein an inner member is completely captured through a slot in an outer member. The open lockbox 13 in present invention has a gap between the flanges 33 that is different from a closed lockbox design. The gap in the open lockbox 13 provides convenient access to install an electrically insulated pivot.

The electrically insulated pivot in the present invention comprises a shoulder washer 29 supporting a lockbox screw 30. The shoulder washer 29 is composed of an electrically insulative material that prevents a short circuit between the members 11 and 12. A large screw cap 31 fits over the head of the lockbox screw 30. A small screw cap 32 fits over the threaded end of the lockbox screw 30.

Each member 11 and 12 is connected to a pole of a bipolar electrosurgical generator. Electrical connectors 22 and 23 are located on the ring handles 20 and 21 to provide a convenient point of connection. The members 11 and 12 are formed of an electrically conductive material, such as stainless steel. The exposed surfaces of the members, except for the connectors 22 and 23 and the seal surfaces 18 and 19, are preferably spray coated with an insulating material.

The characteristics of the bipolar electrosurgical current are determined by the design of the electrosurgical generator. In the preferred embodiment, the generator will have an output wherein the peak-to-peak voltage will not exceed 130 Volts. This is because higher voltages can cause sparking which results in localized burning of tissue which may result in a failure of the tissue weld. The preferred embodiment has the generator capable of producing high frequency output current of at least 2 Amps RMS. High electrical current is important because it heats the tissue sufficiently to melt the collagen. Lower electrical currents will often produce weak tissue welds with low bursting strength.

During operation, the instrument 10 is used to grasp tissue between the seal surfaces 18 and 19. The surgeon squeezes the ring handles 20 and 21 together, causing pressure to be applied to the tissue. The ratchet teeth 26 and 27 are interlocked at the appropriate ratchet setting, depending on the tissue type and tissue thickness. Bipolar electrosurgical current is applied through the instrument and the tissue to cause the tissue to fuse.

The jaws 16 and 17 have a structure and cross-section that resist bending under load. Thus, for purposes of engineering analysis, the shank portions 14 and 15 act as a cantilever supported beam once the seal surfaces 18 and 19 have been mated. The length of this idealized cantilever beam extends from the lockbox screw 30 to the location of the respective ratchet subs 24 or 25. It is possible to model each shank as a cantilever spring having a spring constant. Each ratchet position is designed to transmit a particular closure force to the jaws 16 and 17 against the action of the restoring force of the cantilever spring.

The spring constant is generally a function of Young's Modulus of the shank material, the moment of inertia of the shank, and the length of the shank portion 14 and 15. When the jaws 16 and 17 of the instrument 10 are closed together, each shank 14 and 15 approximates a cantilever-supported beam. It is properly assumed that the deflection of each shank 14 and 15 remains within the linear range of its stress-strain curve. The behavior of such a beam is well known to materials engineers. A large spring constant will result in large closure forces between the seal surfaces 18 and 19. Similarly, a small spring constant will result in a small closure forces between the seal surfaces 18 and 19. The choice of a proper spring constant will depend on the length of the shank 14 or 15 and the distance between ratchet stops 26 and 27.

Experimental results in animal studies suggest that the magnitude of pressure exerted on the tissue by the seal surfaces 18 and 19 is important in assuring a proper surgical outcome. Tissue pressures within a working range of about 3 $kg/cm^2$ to about 16 $kg/cm^2$ and, preferably, within a working range of 7 $kg/cm^2$ to 13 $kg/cm^2$ have been shown to be effective for sealing arteries and vascular bundles. Tissue pressures within the range of about 4 $kg/cm^2$ to about 6.5 $kg/cm^2$ have proven to be particularly effective in sealing arteries and tissue bundles.

It is desirable to tune the spring constant of the shank portions 14 and 15, in conjunction with the placement of the ratchet teeth 26 and 27, such that successive ratchet positions will yield pressures within the working range. In one embodiment, the successive ratchet positions are two millimeters apart.

Pressure on the tissue can be described in several ways. Engineers will recognize that the amount of pressure exerted on the tissue depends on the surface area of the tissue that is in contact with the seal surfaces. In the one embodiment, the width of each seal surface 18 and is in the range of 2 to 5 millimeters, and preferably 4 millimeters width, while the length of each seal surface 18 and 19 is preferably in the range of 10 to 30 millimeters. It has been found through experimentation that at least one interlocking ratchet position preferably holds the closure force between approximately 400 and 650 grams per millimeter of seal surface width. For example, if the width of the seal surface 18 and 19 is 4 millimeters, the closure force is preferably in the range of 1600 grams to 2600 grams. In one embodiment, the closure force is 525 grams per millimeter of width, yielding a closure force of 2100 grams for a 4 millimeter width seal surface 18 and 19.

It has been found experimentally that local current concentrations can result in an uneven tissue effect, and to reduce the possibility of this outcome, each seal surface 18 and 19 has a radiused edge in the preferred embodiment. In addition, a tapered seal surface 18 and 19 has been shown to be advantageous in certain embodiments because the taper allows for a relatively constant pressure on the tissue along the length of the seal surfaces 18 and 19. The width of the seal surfaces 18 and 19 is adjusted, in certain embodiments, wherein the closure force divided by the width is approximately constant along the length.

In one embodiment, a stop 37, made from insulative material, is located in the instrument to maintain a minimum separation of at least about 0.03 millimeters between the seal surfaces 18 and 19, as shown in FIG. 1. The stop 37 reduces the possibility of short circuits between the seal surfaces 18 and 19. In another embodiment, the forceps instrument 10 includes a second or alternative stop 47 which is designed to maintain a minimum separation of at least about 0.03 millimeters between the seal surfaces 18 and 19, as shown in FIG. 1. It is envisioned that the stop may be positioned proximate the lockbox 13, proximate the lockbox screw 30 or adjacent the opposable seal surfaces 18 and 19. Preferably, the stop 37 and/or the stop 47 maintain a separation distance within the range of about 0.03 millimeters to about 0.16 millimeters.

Figure 11A:
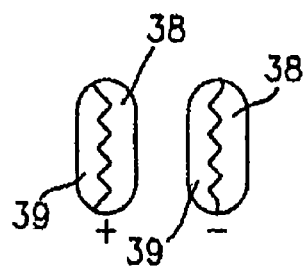
FIGS. 11A and 11B is a top view each of a pair of seal surfaces showing conductive regions and insulative regions that prevent a short circuit when the seal surfaces are mated in opposition.
Figure 11B:
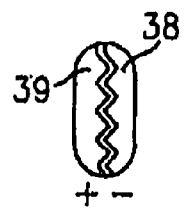

In certain embodiments, as shown in FIG. 11, the seal surfaces 18 and 19 comprise conductive regions 38 and insulative regions 39 arranged such that each conductive region 38 opposes an insulative region 39 when the opposable seal surfaces 18 and 19 are mated in opposition. The seal surfaces 18 and 19, in certain embodiments, may be removable from its respective member 11 or 12 by standard mechanical interfaces, such as a pin and socket arrangement.

Figure 2:
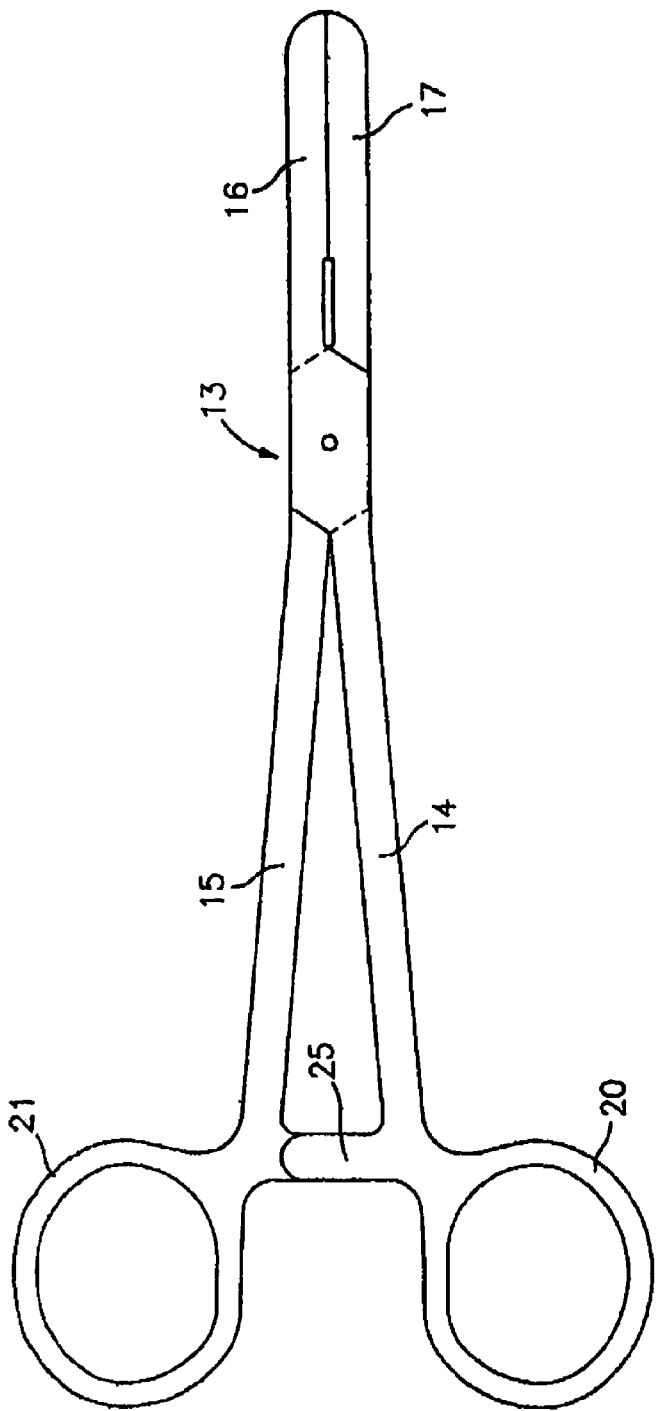
FIG. 2 is a schematic plan view of a bipolar instrument for vessel fusion having a longer curved jaw.
Figure 3:
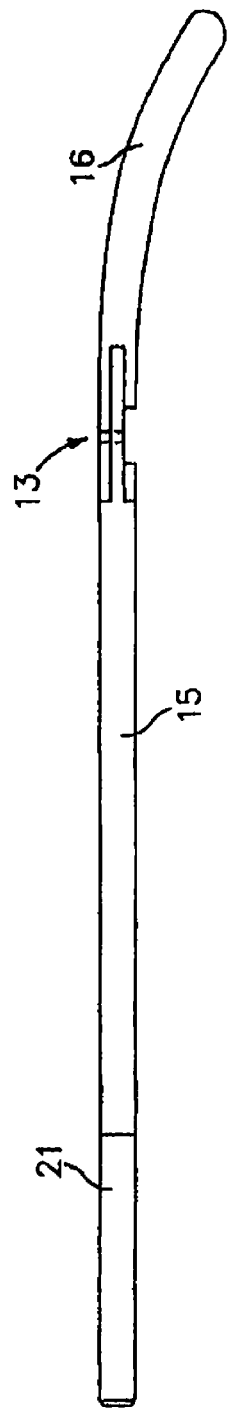
FIG. 3 is a side view of the instrument shown in FIG. 2.
Figure 6:
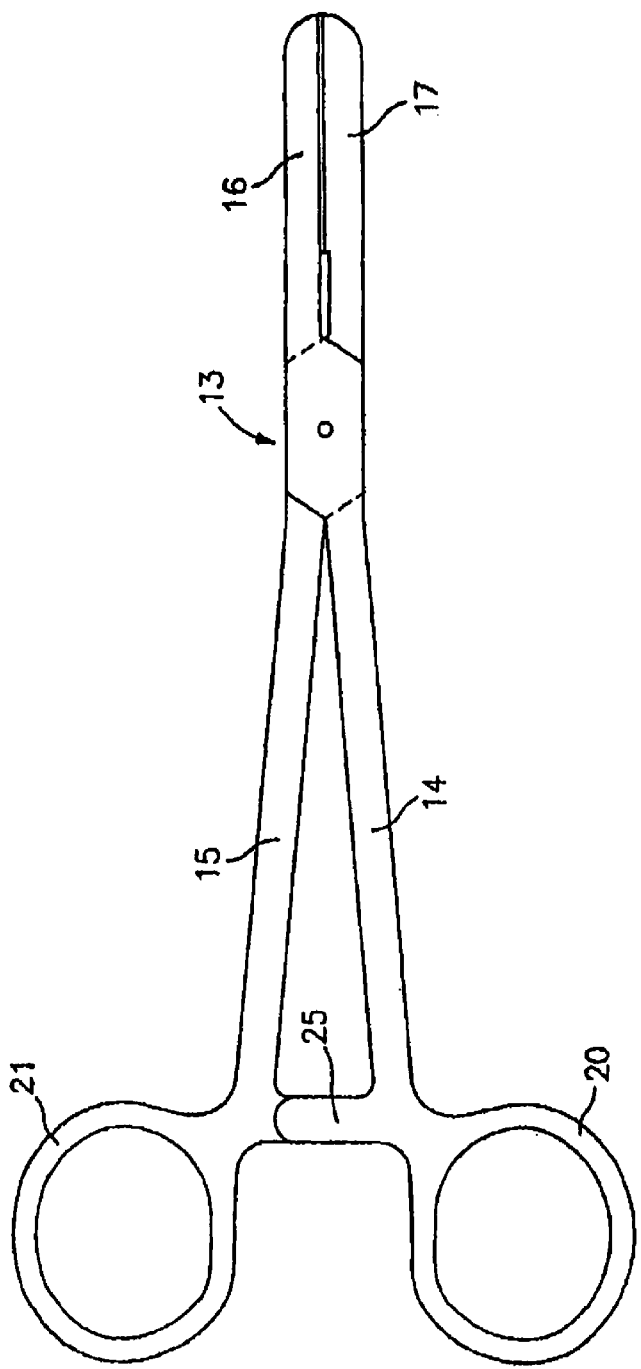
FIG. 6 is a schematic plan view of an alternative embodiment of an instrument for vessel fission having a straight jaw.
Figure 7:
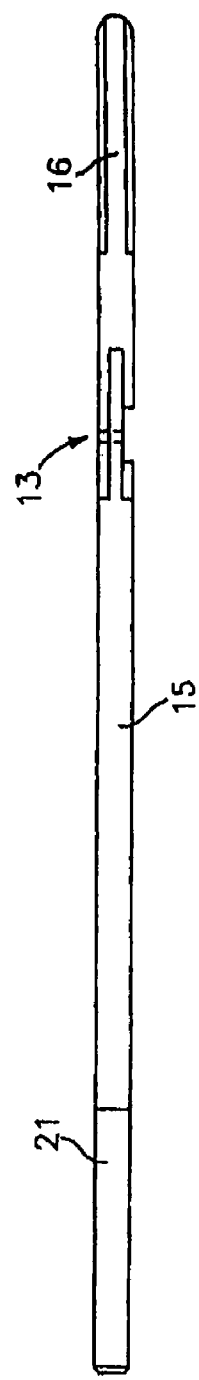
FIG. 7 is a side view of the instrument shown in FIG. 7.

FIG. 2 shows an embodiment for a thirty-two millimeter curved seal surface. FIG. 3 is a side view of FIG. 2. The members 11 and 12 in FIG. 2 are formed from American Iron and Steel Institute (AISI) 410 stainless steel. The length and cross sectional area of the shank portions 14 and 15 are shown in FIGS. 2 and 3 to provide a spring constant of twenty-five pounds per inch deflection.

The embodiment shown in FIGS. 4 and 5 has a twenty millimeter curved seal surface. The embodiment shown in FIGS. 6 and 7 has a thirty-two millimeter straight seal surface. Each embodiment in FIGS. 2 through 7 is designed to have the look and feel of a standard hemostat.

Figure 8:
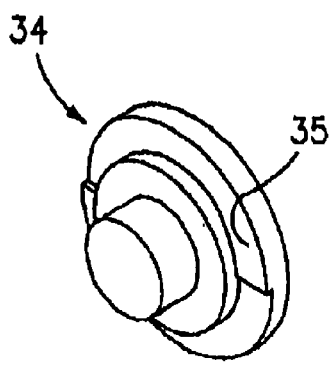
FIG. 8 is a perspective view of a shoulder pin.
Figure 9:
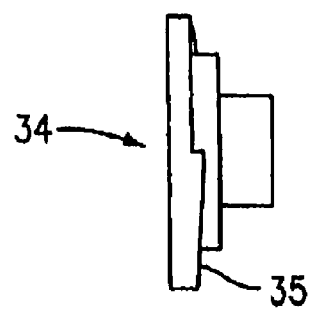
FIG. 9 is a side view of a shoulder pin.
Figure 10:
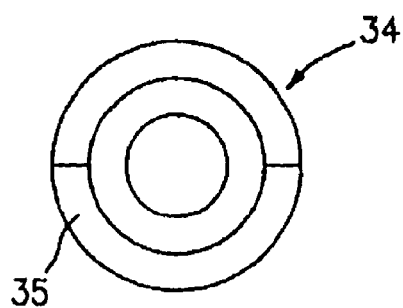
FIG. 10 is a front view of a shoulder pin.

FIGS. 8, 9 and 10 show three views of a shoulder pin 34 that can be used, in certain embodiments, instead of the lockbox screw 30 to connect the members 11 and 12. The shoulder pin 34 has at least one ramp surface 35 that engages one of the members 11 or 12 to cause increasing mechanical interference as the jaws 16 and 17 move toward each other. In one embodiment, the shoulder pin 34 forms part of the open lockbox 13 to aid alignment of the seal surfaces 18 and 19. In another embodiment, the shoulder pin 34 is used without an open-lockbox 13, and movably pins the members 11 and 12 together without a flange 33. The interference fit may require the calibration of the instrument 10 to insure that the applied force will be sufficient to provide the appropriate working pressure between the seal surfaces 18 and 19. A slightly higher spring constant in the shank portions 14 and 15 is preferably used, depending on the level of interference caused by the shoulder pin.

A method of using the bipolar electrosurgical instrument comprises the following steps. A surgeon grasps the ring handles 20 and 21 on the instrument 10 to manipulate the jaws 16 and 17. A vessel or vascular tissue is compressed between the opposable seal surfaces 18 and 19. The opposable seal surfaces 18 and 19 preferably come together in aligned opposition due to the alignment action of the open-lockbox 13, or in certain embodiments due to the alignment action of the shoulder pin 34. The surgeon further deflects the shank portions 14 and 15 of the members 11 and 12 to engage the ratchet teeth 26 and 27. The engagement of the ratchet teeth 26 and 27 hold the shank portions 14 and 15 in their deflected positions to provide a constant spring force that is transmitted as a closure force to the jaws 16 and 17. An electrosurgical generator is connected to the instrument 10 through connectors 22 and 23 on the ring handles 20 and 21. An electrical switch is used to close a circuit between the generator and the instrument 10. The switch may be a footswitch such as Valleylab's catalog number E6009, available from Valleylab Inc., Boulder Colo. The electrosurgical current flows through an electrically conductive path on each of the inner and outer members 11 and 12 between its respective electrical connector, 22 or 23, and its respective seal surface, 18 or 19. An electrically insulative coating 36 substantially covers each member 11 and 12 to protect the surgeon against electrical arcs. An insulative sheath may also be used to cover the members or the component parts thereof, i.e., handles 20, 21, shanks 14 and 15 and the outer surfaces (non-opposing surfaces) of the jaw members 16, 17.

It is envisioned that the outer surface of the jaw members 16 and 17 may include a nickel-based material, coating, stamping, metal injection molding which is designed to reduce adhesion between the jaw members (or components thereof) with the surrounding tissue during activation and sealing. Moreover, it is also contemplated that other components such as the shanks 14, 15 and the ring handles 20, 21 may also be coated with the same or a different "non-stick" material. Preferably, the non-stick materials are of a class of materials that provide a smooth surface to prevent mechanical tooth adhesions.

It is also contemplated that the tissue sealing surfaces 18 and 19 of the jaw members 16 and 17, respectively, may be manufactured from one (or a combination of one or more) of the following "non-stick" materials: nickel-chrome, chromium nitride, MedCoat 2000 manufactured by The Electrolizing Corporation of OHIO, Inconel 600 and tin-nickel. For example, high nickel chrome alloys and Ni200, Ni201 (~100% Ni) may be made into electrodes or sealing surfaces by metal injection molding, stamping, machining or any like process.

In addition these materials preferably include an optimal surface energy for eliminating sticking due in part to surface texture and susceptibility to surface breakdown due electrical effects and corrosion in the presence of biologic tissues. It is envisioned that these materials exhibit superior non-stick qualities over stainless steel and should be utilized on the instrument in areas where the exposure to pressure and RF energy can create localized "hot spots" more susceptible to tissue adhesion. As can be appreciated, reducing the amount that the tissue "sticks" during sealing improves the overall efficacy of the instrument.

The tissue sealing surfaces 18 and 19 may also be "coated" with one or more of the above materials to achieve the same result, i.e., a "non-stick surface". For example, Nitride coatings (or one or more of the other above-identified materials) may be deposited as a coating on another base material (metal or nonmetal) using a vapor deposition manufacturing technique.

One particular class of materials disclosed herein has demonstrated superior non-stick properties and, in some instances, superior seal quality. For example, nitride coatings which include, but are not not limited to: TiN, ZrN, TiAlN, and CrN are preferred materials used for non-stick purposes. CrN has been found to be particularly useful for non-stick purposes due to its overall surface properties and performance. Other classes of materials have also been found to reducing overall sticking. For example, high nickel/chrome alloys with a Ni/Cr ratio of approximately 5:1 have been found to significantly reduce sticking in bipolar instrumentation. One particularly useful non-stick material in this class is Inconel 600. Bipolar instrumentation having electrodes made from or coated with Ni200, Ni201 (~100% Ni) also showed improved non-stick performance over typical bipolar stainless steel electrodes.

It is to be understood that the above described embodiments are only illustrative of the application of the principles of the present invention. Numerous modifications and alternative arrangements may be devised by those skilled in the art without departing from the spirit and scope of the present invention. The appended claims are intended to cover such modifications and arrangements.

What is claimed is:

1. A bipolar electrosurgical instrument, comprising:
   inner and outer members each including a jaw member having an opposable seal surface disposed thereon, the inner and outer members being movable from a first position wherein the opposable seal surfaces are disposed in spaced-apart relation relative to one another to a second position to facilitate grasping tissue between the opposable seal surfaces;
   at least one connector in electrical communication with the opposable seal surfaces and adapted to electrically couple the opposable seal surfaces to a source of electrosurgical energy to facilitate conducting electrosurgical energy through tissue disposed therebetween during usage of the instrument; and
   a ratchet disposed on one of the inner and outer members and at least one complementary interlocking mechanical interface disposed on the other of the inner and outer members, at least one of the ratchet and the interlocking mechanical interface selectively engageable with one of the inner and outer members and configured to insulate the inner and outer members from one another, the ratchet and the complementary interlocking mechanical interface defining at least one interlocking position to maintain a closure pressure in the range of about 3 kg/cm$^2$ to about 16 kg/cm$^2$ between opposable seal surfaces.

2. A bipolar electrosurgical instrument according to claim 1 wherein at least one of the ratchet and the interlocking mechanical interface is configured to selectively engage a respective ratchet stub disposed on one of the inner and outer members in a press-fit manner.

3. A bipolar electrosurgical instrument according to claim 1 wherein both the ratchet and the complementary interlocking mechanical interface are selectively engageable with a respective one of the inner and outer members and configured to insulate the inner and outer members from one another.

4. A bipolar electrosurgical instrument according to claim 1 including at least one stop member disposed adjacent to at least one of the opposable seal surfaces to maintain a separation distance between the opposable seal surfaces when the inner and outer members are moved to the second position.

5. A bipolar electrosurgical instrument according to claim 1 wherein at least one of the opposable seal surfaces includes a non-stick coating disposed thereon which reduces tissue adhesion during the sealing process, the non-stick material being deposited on the opposable seal surfaces and including one of TiN, ZrN, TiAlN, CrN, nickel/chrome alloys with a Ni/Cr ratio of approximately 5:1, Inconel 600, Ni200 and Ni201.

6. A bipolar electrosurgical instrument according to claim 1 wherein the inner and outer members are movable about a lockbox screw which is supported by an insulative shoulder washer, the insulative shoulder washer configured to insulate the inner and outer members from one another through the range of motion from the first and second positions.

7. A bipolar electrosurgical instrument according to claim 6 wherein the shoulder washer includes a ramped surface configured to increase the mechanical interference between the inner and outer members through the range of motion from the first to second positions.

8. A bipolar electrosurgical instrument according to claim 1 wherein the closure pressure is in the range of about 4 kg/cm$^2$ to about 6.5 kg/cm$^2$.

9. A bipolar electrosurgical instrument according to claim 1 wherein the ratchet and the interlocking mechanical interface include several selectable levels of pressure ranging from a high level of pressure for sealing large vessels to a lower level of pressure for sealing smaller vessels, 10. A bipolar electrosurgical instrument according to claim 1 wherein each of the opposable sealing surfaces includes a conductive region and an insulative region and wherein at least one conductive region of one of the sealing surfaces opposes at least one insulative region of the other of the sealing surfaces.

11. A bipolar electrosurgical instrument according to claim 1 wherein at least one of the opposable sealing surfaces is removably engageable with one of the inner and outer members.

12. A bipolar electrosurgical instrument according to claim 1 further comprising an insulative coating disposed on at least one of the inner and outer members.

13. A bipolar electrosurgical instrument according to claim 1 wherein the inner and outer members include curved jaw members disposed at a distal end thereof and handles disposed at a proximal end thereof.

* * * * *